US006864251B2

(12) United States Patent
Kucharik et al.

(10) Patent No.: US 6,864,251 B2
(45) Date of Patent: Mar. 8, 2005

(54) TREATMENT OF LTB₄-MEDIATED INFLAMMATORY DISORDERS WITH OPTICALLY-PURE (R)-2,3-BENZODIAZEPINES

(75) Inventors: Robert F. Kucharik, Glenmoore, PA (US); Herbert W. Harris, Merion, PA (US)

(73) Assignee: Vela Pharmaceuticals, Inc., Lawrenceville, NJ (US)

( * ) Notice: Subject to any disclaimer, the term of this patent is extended or adjusted under 35 U.S.C. 154(b) by 17 days.

(21) Appl. No.: 10/309,573

(22) Filed: Dec. 3, 2002

(65) Prior Publication Data

US 2004/0106602 A1 Jun. 3, 2004

(51) Int. Cl.⁷ .............................................. A61K 31/55

(52) U.S. Cl. ....................... 514/221; 514/219; 514/220; 514/825; 514/863; 514/886

(58) Field of Search ................................ 514/221, 825, 514/863, 886, 219, 220

(56) References Cited

U.S. PATENT DOCUMENTS

| | | | |
|---|---|---|---|
| 3,736,315 A | 5/1973 | Kórósi et al. | 540/567 |
| 4,322,346 A | 3/1982 | Kórósi et al. | 540/567 |
| 4,423,044 A | 12/1983 | Kórósi et al. | 514/221 |
| 4,614,740 A | 9/1986 | Láng et al. | 514/221 |
| 4,835,152 A | 5/1989 | Kórósi et al. | 514/220 |
| 4,840,948 A | 6/1989 | Láng et al. | 514/221 |
| 5,204,343 A | 4/1993 | Andrási et al. | 514/221 |
| 5,288,863 A | 2/1994 | Somogyi et al. | 540/567 |
| 5,459,137 A | 10/1995 | Andrási et al. | 514/220 |
| 5,519,019 A | 5/1996 | Andrási et al. | 514/220 |
| 5,521,174 A | 5/1996 | Andrási et al. | 514/220 |
| 5,639,751 A | 6/1997 | Andrási et al. | 514/220 |
| 5,891,871 A | 4/1999 | Xia et al. | 514/219 |
| 6,075,018 A | 6/2000 | Vágó et al. | 514/221 |
| 6,080,736 A | 6/2000 | Landry | 514/221 |
| 6,638,928 B1 * | 10/2003 | Harris et al. | 514/221 |
| 6,649,607 B2 * | 11/2003 | Leventer et al. | 514/221 |

FOREIGN PATENT DOCUMENTS

| | | |
|---|---|---|
| EP | 0 492 485 A1 | 7/1992 |
| HU | 178516 | 3/1983 |
| WO | WO 92/11262 | 7/1992 |
| WO | WO 00/24400 | 5/2000 |

OTHER PUBLICATIONS

Don E. Griswold et al., "Technique for Quantification of LTB₄–Induced Changes in Peripheral Granulocyte Counts In Vivo in the Rabbit", Journal of Pharmacological Methods 25, 319–328 (1991).

F. Gatta et al., "Derivatives of 2,3–Benzodiazepine (*)", II Farmaco—Ed. Sc.—vol. 40—fasc. 12, pp. 942–955.

R. Sladká et al., "A Placebo–controlled Clinical Trial with Tofizopam * in the Treatment of Anxiety Neurosis" Divisions of Psychiatry, District Institutes of National Health, Prague, 2 and 4; Psychiatric Department and Psychiatric Research Unity, Medical Scholl of Charles University, Prague, Czechoslovakia, pp. 176–180.

Edit J. Horváth et al., "Anxiolytic 2,3–benzodiazepines, their Specific Binding to the Basal Ganglia", Progress in Neurobiology vol. 60 (2000), pp. 309–342.

E. Tomori et al., "Investigation of the Metabolites of Tofizopam in Man and Animals by Gas–Liquid Chromatography–Mass Spectrometry", Journal of Chromatography, 241 (1982), pp. 89–99.

Eva Tomori et al., "Investigation of Metabolites of Tofizopam in Man and Animals", Polish Journal of Pharmacology and Pharmacy, 1984, 36, pp. 423–430., PL ISSN 0301–0214.

Sharon Pellow et al., "The Effects of Tofisopam, a 3,4–Benzodiazepine in Animal Models of Anxiety, Sedation, and Convulsions", Drug Development Research 7, pp. 61–73 (1986).

A. Bond et al., "A Comparison of the Psychotropic Profiles of Tofisopam and Diazepam", Fur J Clin Pharmacol (1982) 22, pp. 137–142.

B.S. Tsai et al., "The Leukotriene B₄ Receptor Agonist/Antagonist Activities of SC–45694 in Human Neutrophils", The Journal of Pharmacology and Experimental Therapeutics, vol. 268, No. 3, 1994, pp. 1493–1498.

Olu Oyesanmi, M.D. et al., "Hematologic Side Effects of Psychotropics", Psychosomatics 1999 40, pp. 414–421.

J. Kanto et al., "Tofizopam: A Benzodiazepine Derivative Without Sedative Effect", International Journal of Clinical Pharmacology, Therapy and Toxicology, vol. 20 No. 7—1982, pp. 309–312.

(List continued on next page.)

*Primary Examiner*—Kevin E. Weddington
(74) *Attorney, Agent, or Firm*—Drinker Biddle & Reath LLP

(57) ABSTRACT

Compounds according to formula I:

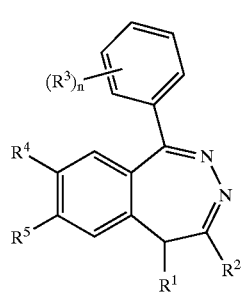

wherein $R^1$, $R^2$, $R^3$, $R^4$, $R^5$ and n are as defined herein, are administered for the treatment of inflammatory disorders mediated by $LTB_4$.

12 Claims, 3 Drawing Sheets

OTHER PUBLICATIONS

T. Mennini et al., "Brain Levels of Tofizopam in the Rat and Relationship with Benzodiazepine Receptors", Naunyn-Schmiedeberg's Arch Pharmacol (1982) 321, pp. 112–115.

K. Maier et al., "The Effect of Tofisopam on Psychic Performance in Persons with More than Average Anxiety: A Controlled Experimental Trial", Current Therapeutic Research, vol. 35, No. 4, Apr. 1984, pp. 541–548.

Chihiro ITO, Behavioral Pharmacological Study of the Structure–Activity Relationship of Benzodiazepine Derivatives—with Particular Reference to the Activity of 2,3–Benzodiazepine–, (1981) 39(3), pp. 369–384 (Japanese), pp. 1–30 (English Translation).

Milena Rizzo, "Chromatographic Separation of 2, 3–Benzodiazepines", Journal of Chromatography B, 747 (2000), pp. 203–216.

Miklos Simonyi et al, "Stereoselective Binding of a 2,3–Benzodiazepine to Human Serum Albumin", Biochemical Pharmacology, vol. 32, No. 12, (1983), pp. 1917–1920.

Giovambattista De Sarro et al., "GYKI 52466 and Related 2,3–Benzodiazepines as Anticonvulsant Agents in DBA/2 Mice", European Journal of Pharmacology 294 (1995), pp. 411–422.

T. Seppälä, "Tofisopam, A Novel 3,4–Benzodiazepine: Multiple–Dose Effects on Psychomotor Skills and Memory. Comparison with Diazepam and Interactions with Ethanol", Psychopharmacology 69, (1980), pp. 209–218.

Veijo Saano et al., "Tofizopam Modulates the Affinity of Benzodiazepine Receptors in the Rat Brain", Pharmacology Biochemistry & Behavior, vol. 17, (1982), pp. 367–369.

Sharon Pellow et al., "The Effects of Tofisopam, a 3,4–Benzodiazepine, in Animal Models of Anxiety, Sedation, and Convulsions", Drug Development Research 7 (1986), pp. 61–73.

A. Pakkanen et al., "Comparative Study of the Clinical Effects of Tofizopam, Nitrazepam and Placebo as Oral Premedication", British Journal of Anaesthesics, pp. 1009–1012.

V. Saano et al., "Tofizopam Enhances the Action of Diazepam Against Tremor and Convulsions", Medical Biology 61: (1983), pp. 49–53.

V. Saano et al., "Tofizopam Selectively Increases the Action of Anticonvulsants", Medical Biology, 64 (1986), pp. 201–206.

E.–E. Claesson, "Stimulation of Human Myclopoiesis by Leurotriese 8", Biochemical and Biophysical Research Communications, vol. 131, No. 2 (1985), pp. 579–585.

Julia Visy et al., "The Role of Configuration and Conformation in the Binding of 2,3–Benzodiazepines to Human Serum Albumin", CHIRALITY 1 (1989), pp. 271–275.

István Tarnawa et al., "Structure–Activity Relationships of 2,3–Benzodiazepine Compounds with Glutamate Antagonistic Action", Bioorganic & Medical Chemistry Letters, vol. 3, No. 1, (1993), pp. 99–104.

Sergey V. Kalashnikov et al., "Immunomodulating Effects of Tofizopam (Grandaxin®) and Diazepam in Vitro", Mediators of Inflammation, vol. 11, (2002), pp. 53–59.

Fogassy E. et al., "Studies on the Properties and Structure of Optically Active 1–(3, 4–Dimethoxyphenyl)–4–Methyl–5–Ethyl–7, 8–Dimethoxy–5H–2,3–Benzodiazepine (Tofisopam)", Studies in Organic Chemistry, vol. 18, (1984), pp. 229–233.

Mark A. Jagels et al., "Neutrophil Chemotactic Factors Promote Leukocytosis", The Journal of Immunology, vol. 148, No. 4, Feb. 1992, pp. 1119–1128.

K. Yamaguchi et al., "Tofisopam, A New 2,3–Benzodiazepine. Inhibition of Changes Induced by Stress Loading and Hypothalamic Stimulation", Can. J. Physiol Pharmaco, vol. 61, (1983), pp. 619–625.

Szegó Judit et al., Selected Passages From the Clinical–Pharmacological and Clinical Trials of Grandaxin®, Acta Pharmaceutica Hungarica vol. 63, (1993), pp. 91–98 (Hungarian). pp. 1–10 (English Translation).

L. Petócz et al., The Main Pharmacological Characteristics of Grandaxin (Tofisopam, Egyt–341), Hungarian Medical Journal, vol. 23, No. 4, (1975), pp. 134–138.

Petócz Luijza, "The Pharmacological Effects of Tofizopam (Grandaxin)®", Acta Pharmaceutica Hungarica, vol. 63, (1993), pp. 72–82 (Hungarian, pp. 1–4 (English Translation).

* cited by examiner

IC/$_{50}$K$_i$ Determination in LTB$_4$ binding of (R)-tofisopam

$IC_{50}K_i$ Determination in $LTB_4$ binding of racemic tofisopam

IC/$_{50}$K$_i$ Determination in LTB$_4$ binding of (S)-tofisopam

TREATMENT OF LTB$_4$-MEDIATED INFLAMMATORY DISORDERS WITH OPTICALLY-PURE (R)-2,3-BENZODIAZEPINES

FIELD OF THE INVENTION

The present invention relates to methods of treatment for inflammatory disorders, particularly disorders mediated by leukotriene B$_4$.

BACKGROUND OF THE INVENTION

Leukotriene B$_4$ (LTB$_4$)

Leukotriene B$_4$ is produced by leukocytes, particularly macrophage and monocytes upon activation by immune complexes, phagocytosis or other stimuli. In this process, membrane phospholipids are broken down by phospholipase A$_2$ to release arachidonic acid, which is further metabolized via one of two pathways. The first is via cycloxygenases to produce prostaglandins. The second is via lipoxygenases to form leukotriene A$_4$ (LTA$_4$). LTA$_4$ is converted to LTB$_4$ or LTC$_4$. LTB$_4$ is a potent chemotactic agent that stimulates neutrophil and macrophage migration (chemotaxis) to sites of inflammation. The structure of LTB$_4$ is shown below.

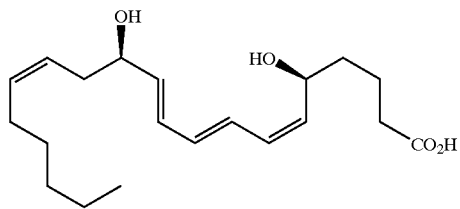

The known pathophysiological responses of LTB$_4$ include: induction of potent neutrophil chemotactic activity, promotion of adhesion of polymorphonuclear leukocytes (PMN's) to vasculature, increase in vascular permeability, stimulation of the release of lysosomal enzymes, by PMN's. The pro-inflammatory action of LTB$_4$ has been demonstrated in vivo, wherein topical LTB$_4$ on human skin promotes the infiltration of PMN's and other inflammatory cells. Intradermal injection of LTB$_4$ induces accumulation of neutrophils at the injection site. Intravenous injection of LTB$_4$ causes rapid but transient neutropenia (Kingsbury et al., *J. Med. Chem.*, 1993, 36, 3308–3320; and references cited therein).

In addition, the presence of physiologically relevant LTB$_4$ concentration at inflammatory sites has been associated with, for example, disease states such as psoriasis, asthma and active gout; in colonic mucosa associated with inflammatory bowel disease; in synovial fluid from patients with active rheumatoid arthritis; and in reperfusion injury. All of these observations together support the involvement of LTB$_4$ in human inflammatory disease (Kingsbury et al, and Griffeths et al., *Proc. Natl. Acad. Sci.* Vol. 92, pp517–521, January 1995; and references cited therein.).

LTB$_4$ is believed to interact with two sub-groups of receptor: a high-affinity receptor and a low-affinity receptor. Research indicates that the high-affinity receptor mediates chemotaxis and that the low-affinity receptor mediates LTB$_4$-induced secretory and oxidase-activation responses (Yokomizo et al. 2000). Some LTB$_4$ antagonists are observed to antagonize all LTB$_4$ mediated activity. Other LTB$_4$ antagonists modulate only the activity associated with one but not the other sub-population of LTB$_4$ receptors.

LTB$_4$ Antagonists

Compounds, which act as antagonists of LTB$_4$ include, for example: structural analogs of LTB$_4$ such as LTB$_4$-dimethyl amide and 20-CF$_3$-LTB$_4$; SM-9064; U-75302; Ly-223982; SC-41930; ONO 4057 (Prostaglandins, 44(4):261–275, 1992); RG-14893; (E)-3-[2-[6-[3-(3-butoxyphenyl)-3-hydroxypropenyl]pyridin-2-yl]-1-hydroxyethyl]benzoate-benzoic acid, lithium salt (Kingsbury J. Med. Chem, 1993, 36, 3308–3320, and references cited therein); the natural product Leucettamine A and a structural analog, 1-methyl-2-amino-4-[[4'-[4"-(hydroxybutyl)phenyl]methyl]-5-(phenyl-methyl)imidazole (Boehm et al, *J. Med. Chem,* 1993, 36, 22, 3333–3340); a series of pyridine-2-acrylic acids (Kingsbury et al., *J. Med. Chem.,* 1993, 36, 22, 3321–3332); SC-45694 (Tsai et al, *J. Pharm.Exp.Ther.,* 268, 3, 1493–1498); a series of essential fatty acids (Yagaloff et al., *Prostaglandins, Leukotrienes and Essential Fatty Acids* (1995), 52, 293–297); and FPL 55712 and FPL 55231 (Cheng et al., *J. Pharm. Exp. Ther.,* 236(1), 1985). The structures of these compounds show many similarities to the structure of LTB$_4$.

2,3-Benzodiazepines

Certain 2,3-benzodiazepines have been explored extensively for their potent CNS modulating activity. Compounds such as tofisopam (Grandaxin®), girisopam, and norisopam have demonstrated substantial anxiolytic and antipsychotic activity.

Tofisopam has been shown in humans to have an activity profile that is significantly different from that of widely used 1,4-benzodiazepine (BZ) anxiolytics such as diazepam (Valium®) and chlordiazepepoxide (Librium®). The 1,4-benzodiazepine, in addition to having sedative-hypnotic activity, also possess muscle relaxant and anticonvulsant properties which, though therapeutically useful in some disease states, are nonetheless potentially untoward side effects. Thus, the 1,4-benzodiazepines, though safe when administered alone, may be dangerous in combination with other CNS drugs including alcohol.

Tofisopam, in contrast, is a non-sedative anxiolytic that has no appreciable sedative, muscle relaxant or anticonvulsant properties (Horvath et al., *Progress in Neurobiology,* 60 (2000), 309–342). In clinical studies, tofisopam improved rather than impaired psychomotor performance and showed no interaction with ethanol (Id.). These observations comport with data that show that tofisopam does not interact with central BZ receptors and binds only weakly to peripheral BZ receptors. Additional studies have shown that tofisopam enhances mitogen-induced lymphocyte proliferation and IL-2 production in vitro.

Other 2,3-benzodiazepines that are structurally similar to tofisopam have been investigated and shown to have varying activity profiles. For example, GYKI-52466 and GYKI-53655 (structures shown below) act as noncompetitive glutamate antagonists at the AMPA (α-amino-3-hydroxy-5-methyl-4-isoxazolepropionic acid) site, and have demonstrated neuroprotective, muscle relaxant and anticonvulsant activity (Id.). Another group of 2,3-benzodiazepines that have been investigated are represented by the compound GYKI-52895, and show activity as selective dopamine uptake inhibitors with potential use in antidepressant and anti-Parkinsonism therapy.

Tofisopam (structure shown below), with the atom numbering system indicated) is a racemic mixture of (R)- and (S)-enantiomers. This is due to the asymmetric carbon, i.e., a carbon with four different groups attached, at the 5-position of the benzodiazepine ring.

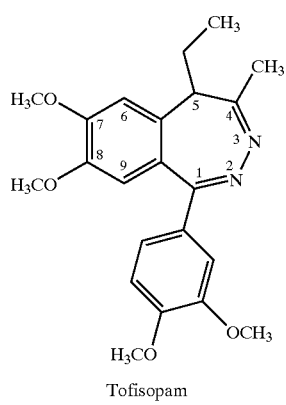

Tofisopam

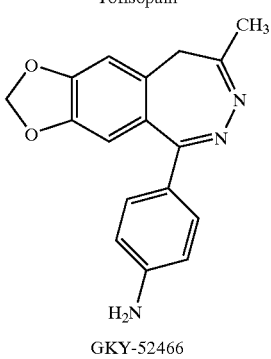

GKY-52466

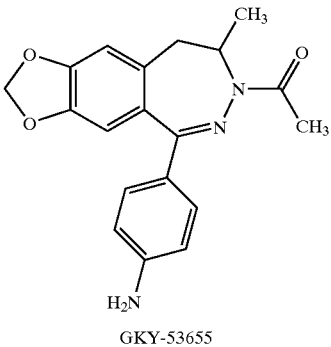

GKY-53655

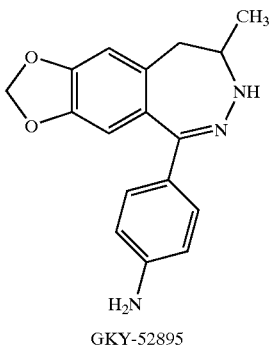

GKY-52895

The molecular structure and conformational properties of tofisopam have been determined by NMR, CD and x-ray crystallography (Visy et al., *Chirality* 1:271–275 (1989)). The 2,3-diazepine ring exists as two different conformers. The major tofisopam conformers, (+)R and (−)S, contain a 5-ethyl group in a quasi-equatorial position. The 5-ehtyl group is positioned quasi-axially in the minor conformers, (−)R and (+)S. Thus, racemic tofisopam can exist as four molecular species, i.e., two enantiomers, each of which exists as two conformations. The sign of the optical rotation is reversed upon inversion of the diazepine ring from one conformer to the other. In crystal form, tofisopam exists only as the major conformations, with dextrorotatory tofisopam being of the (R) absolute configuration. (Toth et al., *J. Heterocyclic Chem.*, 20:709–713 (1983); Fogassy et al., *Bioorganic Heterocycles*, Van der Plas, H. C., Ötvös, L, Simongi, M., eds. Budapest Amsterdam: Akademia; Kiado-Elsevier, 229:233 (1984)).

Differential binding of the (+) and (−) conformations of tofisopam has been reported in binding studies with human albumin (Simongi et al. *Biochem. Pharm.*, 32(12), 1917–1920, 1983). The two (+/−) conformers have also been reported as existing in equilibrium (Zsila et al., *Journal of Liquid Chromatography & Related Technologies*, 22(5), 713–719, 1999; and references therein).

The optically pure (R)-enantiomer of tofisopam (R)-1-(3, 4-dimethoxyphenyl)-4-methyl-5-ethyl-7,8-dimethoxy-5H-2,3-benzodiazepine) has been isolated and shown to possess the nonsedative anxiolytic activity of the racemic mixture. See U.S. Pat. No. 6,080,736; the entire disclosure of which is incorporated herein by reference.

Inflammatory Disorders

Crohn's disease and ulcerative colitis, collectively referred to as inflammatory bowel disease (IBD), are chronic recurrent inflammatory diseases of unclear etiology, affecting the small intestine and colon. Inflammatory bowel disease (IBD) can involve either or both the small and large bowel. These disorders fall into the category of "idiopathic" inflammatory bowel disease because the etiology for them is unknown.

Pathologic findings are generally not specific, although they may suggest a particular form of IBD. "Active" IBD is characterized by acute inflammation. "Chronic" IBD is characterized by architectural changes of crypt distortion and scarring. The term "crypt" refers to a deep pit that protrudes down into the connective tissue surrounding the small intestine. Crypt abscesses (active IBD characterized by the presence of neutrophils in crypt lumens) can occur in many forms of IBD, not just ulcerative colitis. Under normal conditions the epithelium at the base of the crypt is the site of stem cell proliferation and the differentiated cells move upwards and are shed 3–5 days later at the tips of the villi. This normal process, necessary for proper bowel function, is interrupted by IBD Ulcerative colitis (UC) involves the colon as a diffuse mucosal disease with distal predominance. The rectum is virtually always involved, and additional portions of colon may be involved extending proximally from the rectum in a continuous pattern. Most often ulcerative colitis occurs in young people 15 to 40 years of age. Ulcerative colitis occurs only in the inner lining of the colon (large intestine) or rectum. When it is localized in the rectum, it is called "proctitis".

Crohn's Disease is a chronic inflammatory disease that has periods of remission (time when person feels well) and relapse (when a person feels ill). Crohn's disease is an inflammation and ulceration process that occurs in the deep layers of the intestinal wall. The most common areas affected are the lower part of the small intestine, called the ileum, and the first part of the colon. This type of Crohn's disease is called ileocolitis. Crohn's disease can infrequently affect any part of the upper gastrointestinal tract. Aphthous ulcers, which are similar to cold sores, are common. Ulcers can also occur in the esophagus, stomach and duodenum.

Therapy for IBD has historically included administration of corticosteroids. However drawbacks of long term corticosteroid therapy include masking (or induction) of intestinal perforation, osteonecrosis and metabolic bone disease.

Additional problems relate to development of corticosteroid dependency (Habnauer, New England Journal of Medicine, 334(13), p 841–848, 1996). Aminosalicylates such as sulfasalazine and mesalamine have been used to treat mild or moderately active ulcerative colitis and Crohn's Disease, and to maintain remission (Id at 843). Immunomodulatory drugs such as azathioprine and mercaptopurine have been used in long term treatment for patients with IBD. Common complications with both of these drugs include pancreatitis, which occurs with an incidence of 3–15% of patients, and bone marrow suppression, which requires regular monitoring. More potent immunosuppressive drugs such as cyclosporine and methotrexate have been employed, but toxicity of these drugs limits their use to specific situations of refractory disease states. Other therapeutic approaches include antibiotic therapy and nutritional therapy. Often, therapy involves a combination of the above-described drug therapies in addition to surgical resection of the bowel.

There is no cure for IBD. Ultimately, the chronic and progressive nature of IBD demands a long-term treatment that maximizes the local antiinflammatory effect while minimizing the global systemic effect on the immune system.

Chronic inflammatory disorders such as Crohn's Disease typically demonstrate periods of remission between intervals when the inflammatory is active and requires acute treatment. This is an example of a circumstance wherein it is known beforehand that an individual will develop, or is likely to develop an inflammatory disorder.

Another chronic inflammatory condition believed to be mediated by $LTB_4$ is psoriasis. Psoriasis is a chronic, recurrent, papulosquamous plaque on areas of trauma such as the elbow, knee or scalp, though it may appear elsewhere on the skin. Psoriasis may coexist with *lupus erythematosis* in some individuals. Current treatments include topical administration of psoralens. "Psoralens" refers to a group of substances found in many different plants, especially *psoralea corylifolia*. Psoralens interact with nucleic acids and are also used as research tools. Psoriasis is also treated by long-wave ultraviolet radiation. Neither treatment cures or prevents recurrence of psoriasis symptoms.

Another chronic inflammatory disorder believed to be mediated by $LTB_4$ is rheumatoid arthritis, which is an autoimmune disease of the joints. Rheumatoid arthritis is characterized by the following criteria 1–7, wherein criteria 1–4 are present for more than 6 weeks: (1) morning stiffness in and around joints lasting at least one hour before maximum improvement; (2) soft tissue swelling (arthritis) of three or more joints observed by a physician; (3) swelling (arthritis) of the proximal interphalangeal, metacarpal phalangeal, or wrist joints; (4) symmetric swelling; (5) rheumatoid nodules, i.e., a granulomatous lesion characterized by central necrosis encircled by a palisade of monocytes and an exterior mantle of lymphocytic infiltrate. These lesions present as subcutaneous nodules, especially at pressure points such as the elbow in individuals with rheumatoid arthritis or other rheumatoid disorders; (6) presence of rheumatoid factors, i.e., an autoantibody in the serum of individuals with rheumatoid arthritis; and (7) roentgenographic erosions, i.e., joint lesions visible on an X-ray.

Rheumatoid arthritis is a chronic disorder for which there is no known cure. The major goals of treatment of rheumatoid arthritis are to reduce pain and discomfort, prevent deformities and loss of joint function, and maintain a productive and active life. Inflammation must be suppressed and mechanical and structural abnormalities corrected or compensated by assistive devices. Treatment options include reduction of joint stress, physical and occupational therapy, drug therapy, and surgical intervention.

There are three general classes of drugs commonly used in the treatment of rheumatoid arthritis: non-steroidal anti-inflammatory agents (NSAID's), corticosteroids, and remittive agents or disease modifying anti-rheumatic drugs (DMARD's). NSAID's and corticosteroids have a short onset of action while DMARD's can take several weeks or months to demonstrate a clinical effect. DMARD's include leflunomide (Arava™), etanercept (Enbrel™), infliximab (Remicade™), antimalarials, methotrexate, gold salts, sulfasalazine, d-penicillamine, cyclosporin A, cyclophosphamide and azathioprine. Because cartilage damage and bony erosions frequently occur within the first two years, rheumatologists now move more aggressively to a DMARD agent.

Treatmant of rheumatoid arthritis by chronic administration of a corticosteroid involves the same side effect profile as discussed regarding IBD above. Chronic administration of NSAID's also produces side effects. The most common toxicity of NSAID's is gastrointestinal disturbance. Because prostaglandins play a role in the regulation of renal blood flow and maintenance of glomerular filtration, NSAID's can impair renal function in certain patients. Weight gain and cushingoid appearance is a frequent problem and source of patient complaints. Recent studies have raised concern over the increased cardiovascular risk and accelerated osteoporosis associated with low dose prednisone particularly at doses above 10 mg daily.

Gout is another inflammatory disorder believed to be mediated by $LTB_4$. Gout is characterized by a disturbance of uric-acid metabolism occurring chiefly in males. Gout is characterized by painful inflammation of the joints, especially of the feet and hands, and arthritic attacks resulting from elevated levels of uric acid in the blood and the deposition of urate crystals around the joints. The condition can become chronic and result in deformity.

Gout can present another circumstance wherein it is known beforehand that an individual will or is likely to develop an inflammatory disorder. In the instance of patients undergoing radiotherapy or chemotherapy, the individual may experience a dramatic rise in serum uric acid levels associated with lysis of the tumor mass. Such large increases in uric acid can deposit urate crystals in synovial fluid of joints thereby causing the inflammatory disorder, gout. When such a rise in serum uric acid levels is known to be likely, prophylaxis with an $LTB_4$ antagonist can act to prevent the inflammatory condition of gout.

Radiation-induced gastrointestinal inflammation is another inflammatory disorder believed to be mediated by $LTB_4$. Radiation works by damaging cancer cells, but unfortunately can damage non-diseased tissue as well, causing a typical inflammatory reaction in response. Therapeutic radiation is thus generally applied to a defined area of the subject's body which contains abnormal proliferative tissue in order to maximize the dose absorbed by the abnormal tissue and minimize the dose absorbed by the nearby normal tissue. However, it is difficult (if not impossible) to selectively administer therapeutic ionizing radiation to the abnormal tissue. Thus, normal tissue proximate to the abnormal tissue is also exposed to potentially damaging doses of ionizing radiation throughout the course of treatment. Moreover, some treatments require exposure of the subject's entire body to the radiation, in a procedure called "total body irradiation", or "TBI." The efficacy of radiotherapeutic techniques in destroying abnormal proliferative cells is therefore necessarily balanced by the associated cytotoxic effects on nearby normal cells.

After or during a course of radiotherapy, $LTB_4$-mediated inflammatory processes may be triggered, causing damage to the bowel, and leading to sloughing of the cells of the inner lining of the GI tract. Radiation-induced gastrointestinal inflammation can present another circumstance wherein it is known beforehand that an individual will or is likely to develop an inflammatory disorder. In the instance of patients undergoing radiotherapy, the inflammation, damage and sloughing of the gastrointestinal tract is a predictable side effect of the radiotherapy.

New antiinflammatory agents are needed which are useful in the treatment of inflammatory disorders such as IBD, rheumatoid arthritis, gout, psoriasis and radiation-induced gastrointestinal inflammation. In particular, agents are needed that are appropriate for chronic long-term use in treatment. In addition, agents are needed that are useful in the prevention of $LTB_4$-mediated inflammatory disorders that occur secondary to observable events such as ionizing radiation therapy.

SUMMARY OF THE INVENTION

In one embodiment of the invention there is provided a method of treatment or prevention of inflammatory disorders mediated by $LTB_4$, in particular, inflammatory bowel disease, including Crohn's disease and ulcerative colitis; psoriasis; rheumatoid arthritis; gout and radiation-induced gastrointestinal inflammation. The method comprises administering to the individual an effective amount of at least one compound according to formula I:

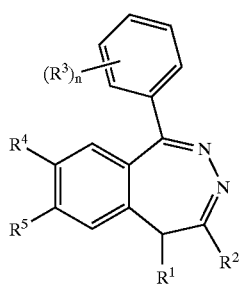

wherein:
$R^1$ is —($C_1$–$C_7$)hydrocarbyl or —($C_2$–$C_6$)heteroalkyl;
$R^2$ is selected from the group consisting of —H, and —($C_1$–$C_7$)hydro-carbyl, wherein $R^1$ and $R^2$ may combine to form a carbocyclic or heterocyclic 5- or 6-membered ring;
$R^3$ is independently selected from the group consisting of —O($C_1$–$C_6$)alkyl, —OH, —O-acyl, —SH, —S($C_1$–$C_3$)alkyl, —$NH_2$, —NH($C_1$–$C_6$)alkyl, —N(($C_1$–$C_6$)alkyl)$_2$, —NH-acyl, —$NO_2$ and halogen;
n is 1, 2 or 3;
$R^4$ and $R^5$ are independently selected from the group consisting of —O($C_1$–$C_6$)alkyl, —OH, O-acyl, —SH, —S($C_1$–$C_3$)alkyl, —$NH_2$, NH-acyl and halogen, wherein $R^4$ and $R^5$ may combine to form a 5, 6 or 7-membered heterocyclic ring; or a pharmaceutically-acceptable salt of such a compound;
wherein the administered compounds according to formula I comprise an R-enantiomer with respect to the absolute conformation at the 5-position of the benzodiazepine ring, and is substantially free of the corresponding S-enantiomer of the same compound.

Preferably, the administered compound of formula I, or a pharmaceutically-acceptable salt of such a compound, comprises 85% or more by weight of the (R)-enantiomer. More preferably, administered compound of formula I, or a pharmaceutically-acceptable salt of such a compound, comprises 90% or more by weight of the (R)-enantiomer. Even more preferably, the administered compound of formula I, or a pharmaceutically-acceptable salt of such a compound, comprises 95% or more by weight of the (R)-enantiomer. Most preferably, the administered compound of formula I, or a pharmaceutically-acceptable salt of such a compound, comprises 99% or more by weight of the (R)-enantiomer.

According to one embodiment of the invention:
$R^1$ is —($C_1$–$C_6$)alkyl;
$R^2$ is selected from the group consisting of —H and —($C_1$–$C_6$)alkyl;
$R^3$ is independently selected from the group consisting of —O($C_1$–$C_6$)alkyl, —O-acyl and —OH;
n is 1, 2 or 3; and
$R^4$ and $R^5$ are independently selected from —O($C_1$–$C_6$)alkyl, —O-acyl and —OH, wherein, $R^4$ and $R^5$ may combine to form a 5, 6 or 7-membered heterocyclic ring; or a pharmaceutically-acceptable salt of such a compound.

According to a preferred embodiment of the invention:
$R^1$ is —$CH_2CH_3$;
$R^2$ is —($C_1$–$C_6$)alkyl;
$R^3$, $R^4$ and $R^5$ are independently selected from the group consisting of —OH and —$OCH_3$; and
n is 1,2 or 3;
or a pharmaceutically-acceptable salt of such a compound.

According to a further preferred embodiment of the invention:
$R^1$ is —$CH_2CH_3$;
$R^2$ is —$CH_3$;
$R^3$, $R^4$ and $R^5$ are independently selected from the group consisting of —OH and —$OCH_3$; and
n is 1, 2 or 3; or a pharmaceutically-acceptable salt of such a compound.

According to a further preferred embodiment of the invention:
$R^1$ is —$CH_2CH_3$;
$R^2$ is —$CH_3$;
$R^3$, $R^4$ and $R^5$ are independently selected from the group consisting of —OH and —$OCH_3$; and
n is 2; or a pharmaceutically-acceptable salt of such a compound.

According to a further preferred embodiment of the invention:
$R^1$ is —$CH_2CH_3$;
$R^2$ is —$CH_3$;
$R^3$, $R^4$ and $R^5$ are independently selected from the group consisting of —OH and —$OCH_3$;
n is 2; and wherein $R^3$ comprises substituents at the 3- and 4-positions of the phenyl ring; or a pharmaceutically-acceptable salt of such a compound.

Preferred compounds according to formula I, for administration, are selected from the group consisting of:
(R)-1-(3,4-dimethoxyphenyl)-4-methyl-5-ethyl-7,8-dimethoxy-5H-2,3-benzodiazepine;
(R)-1-(3,4-dimethoxyphenyl)-4-methyl-5-ethyl-7-hydroxy-8-methoxy-5H-2,3-benzodiazepine;
(R)-1-(3-hydroxy-4-methoxyphenyl)-4-methyl-5-ethyl-7,8-dimethoxy-5H-2,3-benzodiazepine;
(R)-1-(3-methoxy-4-hydroxyphenyl)-4-methyl-5-ethyl-7,8-dimethoxy-5H-2,3-benzodiazepine;
(R)-1-(3,4-dimethoxyphenyl)-4-methyl-5-ethyl-7-methoxy-8-hydroxy-5H-2,3-benzodiazepine;
(R)-1-(3-methoxy-4-hydroxyphenyl)-4-methyl-5-ethyl-7-hydroxy-8-methoxy-5H-2,3-benzodiazepine; and
(R)-1-(3-hydroxy-4-methoxyphenyl)-4-methyl-5-ethyl-7-hydroxy-8-methoxy-5H-2,3-benzodiazepine;

substantially free of the corresponding (S)-enantiomers, or a pharmaceutically-acceptable salt of such a compound.

More preferably, the compound according to formula I, for administration is (R)-1-(3,4-dimethoxyphenyl)-4-methyl-5-ethyl-7,8-dimethoxy-5H-2,3-benzodiazepine, substantially free of the corresponding (S)-enantiomer; or a pharmaceutically-acceptable salt thereof.

The compound, (R)-1-(3,4-dimethoxyphenyl)-4-methyl-5-ethyl-7,8-dimethoxy-5H-2,3-benzodiazepine, the R-enantiomer of tofisopam, is shown in the structure diagram below.

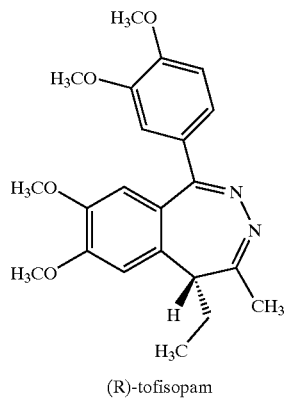

(R)-tofisopam

DEFINITIONS

The term "inflammation" or "inflammatory response" refers to a defense reaction of living tissue to injury. The response serves to contain and to repair the injury. Multiple chemical mediators of inflammation derived from either plasma or cells have been observed. Compounds produced in the metabolism of arachidonic acid, such as prostaglandins and leukotrienes, also affect inflammation, leukotrienes mediating essentially every aspect of acute inflammation.

An "inflammatory disorder mediated by $LTB_4$" or a "$LTB_4$-mediated disorder", refers to a disorder resulting from an inflammatory response wherein $LTB_4$ mediation is implicated as a factor by observation of $LTB_4$ presence at the site of the inflammation.

The term "receptor" refers to a molecular structure or site on the surface or interior of a cell that binds with substances such as hormones, antigens, drugs, or neurotransmitters. An "agonist" at a receptor refers to a drug or other chemical that can bind to a receptor to produce the physiologic reaction that is typical of a naturally occurring substance. An "antagonist" refers to a chemical substance that acts at a receptor to produce a physiologic reaction that is other than the action produced by the natural, endogenous receptor-binding entity or natural ligand. Such antagonist activity may occur when a drug or chemical substance binds the receptor at a much lower concentration than the natural ligand, and thereby displaces the natural ligand and prevents or reduces the amount of receptor binding to the natural ligand.

The term "$LTB_4$ antagonist" means a chemical substance that competitively binds to the $LTB_4$ receptor such that (a) the binding of the natural ligand ($LTB_4$) is inhibited by occupation of the $LTB_4$ receptor by the $LTB_4$ antagonist, and (b) the $LTB_4$ antagonist bound to the $LTB_4$ receptor does not generate the same physiological response produced by native $LTB_4$ bound to the $LTB_4$ receptor.

The term "acyl" means a radical of the general formula —C(=O)—R, wherein —R is hydrogen, hydrocarbyl, amino, alkylamino, dialkylamino hydroxy or alkoxy." Examples include for example, acetyl (—C(=O)CH$_3$), propionyl (—C(=O)CH$_2$CH$_3$), benzoyl (—C(=O)C$_6$H$_5$), phenylacetyl (—C(=O)CH$_2$C$_6$H$_5$), carboethoxy (—CO$_2$CH$_2$CH$_3$), and dimethylcarbamoyl (—C(=O)N(CH$_3$)$_2$). When the R group in the acetyl radical is alkoxy, alkyl amino or dialkyl amino, the alkyl portion is preferably (C$_1$–C$_6$)alkyl, more preferably (C$_1$–C$_3$)alkyl. When the R is hydrocarbyl, it is preferably (C$_1$–C$_7$)hydrocarbyl. When R is hydrocarbyl, it is preferably alkyl, more preferably (C$_1$–C$_6$) alkyl.

The term "alkyl", by itself or as part of another substituent means, unless otherwise stated, a straight, branched or cyclic chain hydrocarbon radical, including di- and multi-radicals, having the number of carbon atoms designated (i.e. C$_1$–C$_6$ means one to six carbons). Alkyl groups include straight chain, branched chain or cyclic groups, with straight being preferred. Examples include: methyl, ethyl, propyl, isopropyl, butyl, isobutyl, tert-butyl, pentyl, neopentyl, hexyl, cyclohexyl and cyclopropylmethyl. (C$_1$–C$_6$)alkyl is preferred. Most preferred is (C$_1$–C$_3$)alkyl, particularly ethyl, methyl and isopropyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$–C$_6$)alkoxy. More preferred is (C$_1$–C$_3$)alkoxy, particularly ethoxy and methoxy.

The term "amine" or "amino" refers to radicals of the general formula —NRR', wherein R and R' are independently selected from hydrogen or a hydrocarbyl radical, or wherein R and R' combined form a heterocycle. Examples of amino groups include: —NH$_2$, methyl amino, diethyl amino, anilino, benzyl amino, piperidinyl, piperazinyl and indolinyl. Preferred hydrocarbyl radicals are (C$_1$–C$_7$)hydrocarbyl radicals. Preferred are hydrocarbyl radicals that are alkyl radicals. More preferred are (C$_1$–C$_6$)alkyl.

The term "aromatic" refers to a carbocycle or heterocycle having one or more polyunsaturated rings having aromatic character (4n+2) delocalized n (pi) electrons).

The term "aryl" employed alone or in combination with other terms, means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "hydrocarbyl" refers to any moiety comprising only hydrogen and carbon atoms. This definition includes for example alkyl, alkenyl, alkynyl, aryl and benzyl groups. Preferred are (C$_1$–C$_7$)hydrocarbyl.

The term "heteroalkyl" by itself or in combination with another term means, unless otherwise stated, a stable straight or branched chain radical consisting of the stated number of carbon atoms and one or two heteroatoms selected from the group consisting of O, N, and S. Nitrogen and sulfur atoms may be optionally oxidized to the N-oxide and sulfoxide or sulfone, respectively. In addition, a nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Preferred are (C$_2$–C$_6$)

heteroalkyl. More preferred are ($C_2$-$C_4$)heteroalkyl. Examples include: —O—$CH_2$—$CH_2$—$CH_3$, —$CH_2$—$CH_2CH_2$—OH, —$CH_2$—$CH_2$—NH—$CH_3$, —$CH_2$—C(=O)—$CH_3$, —$CH_2$—N=N—$CH_2$—$CH_3$, —$CH_2$—S—$CH_2$—$CH_3$, —$CH_2CH_2$—S(=O)—$CH_3$ and —$CH_2$—$CH_2$—NH—$SO_2$—$CH_3$. Up to two heteroatoms may be consecutive, such as, for example, —$CH_2$—NH—$OCH_3$, or —$CH_2$—$CH_2$—S—S—$CH_3$. More preferred are heteroalkyl groups containing one or two oxygen atoms.

When two groups may "combine to form a carbocyclic or heterocyclic 5- or 6-membered ring," a carbocyclic ring is preferably saturated. Preferred heterocyclic rings are saturated rings containing one or two heteroatoms selected from N, O and S. Heterocyclic rings annulated to the benzodiazepine seven-membered ring in this way include, for example, furan, dihydrofuran, tetrahydrofuran, pyran, dihydropyran, tetrahydropyran, thiophene, dihydrothiophene, tetrahydrothiophene, pyrrole, dihydropyrrole, pyrrolidine, pyridine, dihydropyridine, tetrahydropyridine and piperidine.

When two groups may "combine to form a 5-, 6- or 7-membered heterocyclic ring," preferred heterocyclic rings are 5- or 6-membered rings containing one or two heteroatoms selected from N, O and S. More preferred are heterocyclic rings containing one heteroatom selected from N, O and S. Heterocyclic rings annulated to the benzodiazepine phenyl ring in this way include, for example, furan, dihydrofuran, dioxane, dioxolane, pyran, dihydropyran, tetrahydropyran, thiophene, dihydrothiophene, pyridine, dihydropyridine, tetrahydropyridine, piperidine, pyrrole, dihydropyrrole, imidazole, dihydroimidazole, thiazole, dihydrothiazole, oxazole, and dihydrooxazole.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position.

The phrase "optically active" refers to a property whereby a material rotates the plane of plane-polarized light. A compound that is optically active is nonsuperimposable on its mirror image. The property of nonsuperimposablity of an object on its mirror image is called chirality.

The property of "chirality" in a molecule may arise from any structural feature that makes the molecule nonsuperimposable on its mirror image. The most common structural feature producing chirality is an asymmetric carbon atom, i.e., a carbon atom having four nonequivalent groups attached thereto.

The term "enantiomer" refers to each of the two nonsuperimposable isomers of a pure compound that is optically active. Single enantiomers are designated according to the Cahn-Ingold-Prelog system, a set of priority rules that rank the four groups attached to an asymmetric carbon. See March, Advanced Organic Chemistry, $4^{th}$ Ed., (1992), p. 109. Once the priority ranking of the four groups is determined, the molecule is oriented so that the lowest ranking group is pointed away from the viewer. Then, if the descending rank order of the other groups proceeds clockwise, the molecule is designated R and if the descending rank of the other groups proceeds counterclockwise, the molecule is designated S. In the example below, the Cahn-Ingold-Prelog ranking sequence id A>B>C>D. The lowest ranking atom, D is oriented away from the viewer.

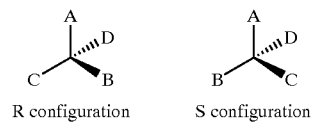

R configuration     S configuration

The term "racemate" or the phrase "racemic mixture" refers to a 50—50 mixture of two enantiomers such that the mixture does not rotate plane-polarized light.).

The term "substantially isolated", or "substantially free" of the other enantiomer or the term "resolved" or the phrase "substantially free" of the corresponding (S)-enantiomer, when used to refer to an optically active compound of formula I, means the (R)- and (S)-enantiomers of the compound have been separated such that the composition is 80% or more by weight a single enantiomer.

Thus, by "(R)-2,3-benzodiazepine substantially free of the (S)-enantiomer" is meant a 2,3-benzodiazepine compound that comprises 80% or more by weight of its (R)-enantiomer and likewise contains 20% or less of its (S)-enantiomer as a contaminant, by weight.

The term "effective amount" when used to describe therapy to a patient suffering from a $LTB_4$-mediated inflammatory disorder, refers to the amount of a compound of formula I that inhibits the inflammatory process, resulting in a therapeutically useful and selective reduction in the symptoms of inflammation when administered to a patient suffering from disorder which manifests chronic or acute inflammation associated with physiologically relevant concentrations of $LTB_4$.

An effective amount of a compound of formula I for the prevention of an $LTB_4$-mediated inflammatory disorder is an amount which prevents or delays the onset of symptoms of an inflammatory disorder in an individual during a time interval coinciding with an increased risk of $LTB_4$-mediated inflammatory disorder.

The term "individual" or "subject", includes human beings and non-human animals. With respect to the disclosed methods of treating $LTB_4$-mediated inflammatory disorders, these terms refer, unless the context indicates otherwise, to an organism that is afflicted with such an inflammatory disorder.

With respect to disclosed methods of preventing $LTB_4$-mediated inflammatory disorders, this term refers unless the context indicates otherwise, to an organism that is likely to be afflicted with such an inflammatory disorder. The selection of an individual likely to incur such an inflammatory disorder may take into account the presence of inflammatory conditions that historically are known to have a high incidence of recurrence, such as, for example, IBD. The likelihood of incurring such an inflammatory disorder may also be due to tissue insult that is known beforehand, such as a surgical procedure. The future inflammatory disorder may also result from a secondary effect of an initial tissue insult. An example of this is inflammation due to gout caused by elevated uric acid levels that occur secondary to lysis of a tumor mass following administration of cytotoxic chemotherapy or therapeutic radiation treatment. The term "prevention" in this context also includes a delay in the onset of inflammation or the symptoms thereof or a prolongation of periods of remission in an individual who experiences recurring inflammatory disorders.

DETAILED DESCRIPTION OF THE INVENTION

Figure 1:
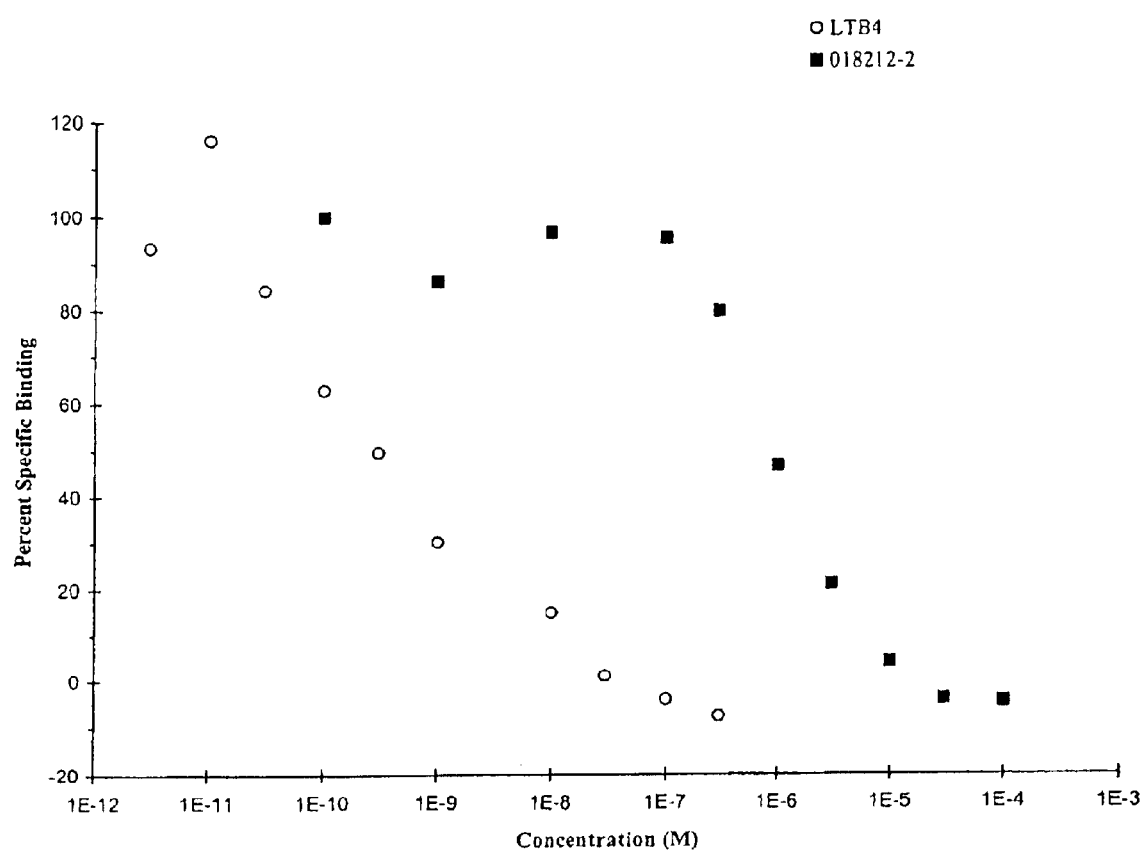
FIG. 1 is a plot of data gathered in a competitive binding study of the displacement of [$^3$H]$LTB_4$ by (R)-tofisopam from LTB$_4$ receptors. IC$_{50}$ and K$_i$ values for (R)-tofisopam displacement of [$^3$H]LTB$_4$ were generated.

According to the present invention, (R)-2,3-benzodiazepines of formula I and pharmaceutically acceptable salts thereof are antagonists of leukotriene B$_4$ and are useful in methods of treatment or prevention of inflammatory disorders mediated by leukotriene B$_4$.

The (R)-2,3-benzodiazepines of formula I useful in the present invention may be prepared by one of several methods. These methods generally follow the synthetic strategies and procedures used in the synthesis of 2,3-benzodiazepines such as tofisopam and tofisopam analogs. See U.S. Pat. Nos. 3,736,315 and 4,423,044 (tofisopam syntheses) and Horvath et al., *Progress in Neurobiology* 60(2000) p.309–342 and references cited therein (preparation of tofisopam and analogs thereof), the entire disclosures of which are incorporated herein by reference. In the synthesis methods that follow, the products of the chemical syntheses are racemic (R)- and (S)-2,3-benzodiazepines. These racemic mixtures are subsequently separated using known methods of resolution to produce the (R)-2,3-benzodiazepines of formula I substantially free of the (S)-enantiomers. By an "(R)-2,3-benzodiazepine" is meant a 2,3-benzodiazepine that has an (R) absolute conformation by virtue of a substitution at the 5-position of the benzodiazepine ring to give a resolvable chiral carbon at the 5-position. By an "(R)-2,3-benzodiazepine substantially free of the (S)-enantiomer" or "an (R)-enantiomer of a compound of formula I substantially free of the corresponding (S)-enantiomer" is meant a compound that comprises 80% or more by weight of the desired (R)-enantiomer and likewise contains 20% or less of the (S)-enantiomer as a contaminant, by weight. Preferably, compounds used in methods of the present invention have a composition that is 85% by weight or greater of the (R)-enantiomer, and 15% by weight, or less, of the (S)-enantiomer. More preferably, compounds used in methods of the present invention have a composition that is 90% by weight or greater of the (R)-enantiomer and 10% by weight, or less, of the (S)-enantiomer. More preferably, compounds used in methods of the present invention have a composition that is 95% by weight or greater of the (R)-enantiomer and 5% by weight, or less, of the (S)-enantiomer. Most preferably, compounds used in methods of the present invention have a composition that is 99% by weight or greater of the (R)-enantiomer and 1% by weight, or less, of the (S)-enantiomer.

Racemic 2,3-benzodiazepines may be synthesized, as shown in Scheme 1, from the corresponding 2-benzopyrylium salt H by reaction with hydrazine hydrate, wherein X$^-$ is a counterion such as, for example perchlorate:

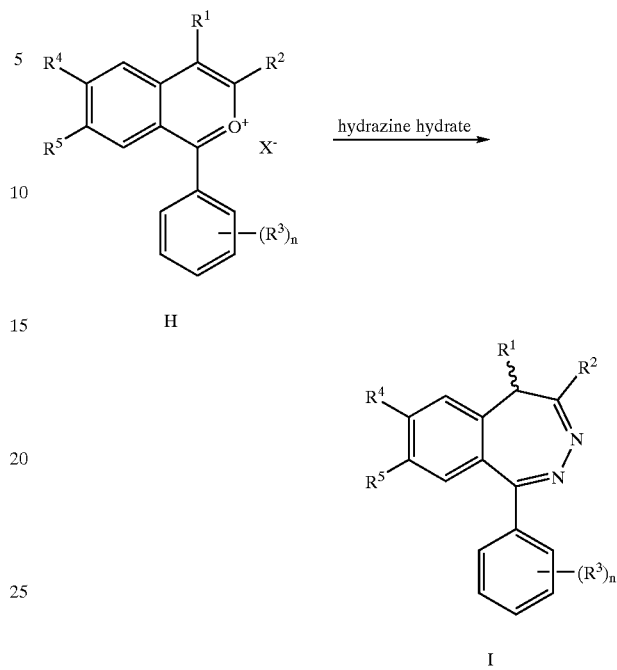

Scheme 1

Accordingly, hydrazine hydrate (98%, approximately 3 equivalents based on the 2-benzopyrylium salt) is added dropwise to a stirred solution of the 2-benzopyrylium salt H in glacial acetic acid (approximately 1 mL/3 mmol of 2-benzopyrylium salt). During this operation, the solution is maintained at an elevated temperature, preferably, 80–100° C. The solution is then maintained a higher elevated temperature, preferably 95–100° C., for about one hour. Then the reaction mixture is diluted with 2% aqueous sodium hydroxide solution (approximately 3 equivalents based on the 2-benzopyrylium salt) and cooled. The product 2,3-benzodiazepine separates as a solid and is removed by filtration, washed with water and dried. The crude product may be purified by taking it up in a polar aprotic solvent such as dimethylformamide (DMF) at an elevated temperature, preferably 100–130° C., and decolorizing the solution with activated carbon. The carbon is removed by filtration and the filtered solution is diluted with water. The purified product precipitates out of the solution and is collected by filtration.

See Kórósi et al., U.S. Pat. No. 4,322,346, the entire disclosure of which is incorporated herein by reference, disclosing three variations of the reaction protocol for preparing a substituted 2,3-benzodiazepine from the precursor benzopyrilium salt.

Retrosynthetically, the intermediate benzopyrilium salt, H, may be prepared from one of several starting materials. According to one such method, illustrated in Scheme 2, intermediate H is prepared from the corresponding aryl ethanol derivative D via the isochroman intermediate F.

Another variation for preparing 2,3-benzodiazepines is illustrated in Scheme 3 and 4 (Examples 2 and 3). The synthesis there proceeds from intermediate G without isolation of the intermediate benzopyrilium salt H.

2-Benzopyrilium salts H may be synthesized from intermediate 2-substituted phenyl ethanol derivatives D through isochroman intermediate F, wherein X$^-$ is a counterion such as, for example, perchlorate:

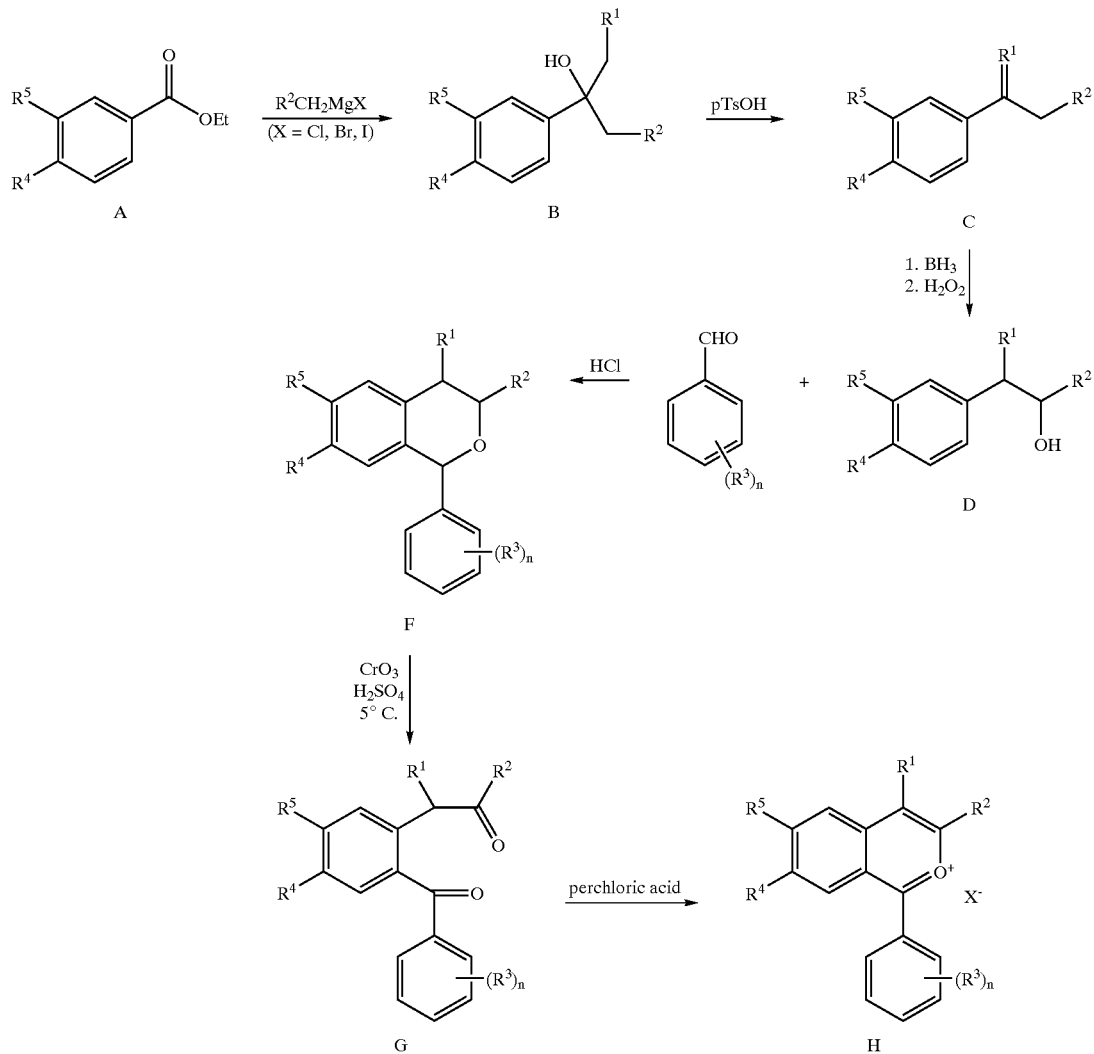

Scheme 2

Accordingly, a substituted benzoic acid ester, A is dissolved in a suitable solvent, preferably ether and cooled to 0° C. Two equivalents of a suitable Grignard reagent are added dropwise and the reaction is allowed to warm to room temperature and monitored for disappearance of starting material. When the reaction is complete, it may be quenched with a proton source such as acetic acid. Volatiles are removed in vacuo, and the product B is used for the next step without purification.

The α,α-substituted benzyl alcohol B is taken up in a high boiling solvent such as toluene and a catalytic amount of para-toluene sulfonic acid (p-TsOH). The mixture is warmed to reflux and may be monitored for disappearance of starting materials. When the reaction is complete, the volatiles are removed in vacuo and the crude product C is purified by column chromatography.

The substituted styrene C is hydroxylated under anti-Markovnikov conditions to give intermediate phenylethyl alcohol D. A solution of D, and of a suitably substituted benzaldehyde E (1.2 eq) are added to anhydrous dioxane. The resulting solution is then saturated with gaseous HCl and warmed, preferably to reflux temperature for about one hour. The mixture is then cooled to room temperature, poured into water, basified (preferably with aqueous sodium hydroxide) and extracted with an organic solvent (preferably ethyl acetate). The extract is dried, filtered and concentrated under vacuum. The resulting residue is purified, preferably by crystallization, to yield F.

To a stirred, cooled, (preferably to 0–5° C.) solution of F (2 g) in acetone (30 mL), is added dropwise a solution of chromium trioxide (2 g) in 35% sulfuric acid (20 mL). The latter solution is added at a rate such that the reaction temperature remains below 5° C. After the addition is complete, the reaction mixture is allowed to rise to room temperature and is stirred at room temperature for two hours. The reaction mixture is then poured into water and extracted with an organic solvent, preferably ethyl acetate. The organic extract is washed with water and then with ice-cold 10% aqueous sodium hydroxide. The aqueous alkaline fraction is then acidified, preferably with dilute aqueous hydrochloric acid, and extracted with an organic solvent, preferably, chloroform. The chloroform extract is dried, filtered and concentrated under vacuum to give G. The crude residue may further be purified by column chromatography.

The 2-α-acyl hydrocarbylbenzophenone G (5 g) is dissolved in glacial acetic acid (15 mL). To this mixture is added 60% perchloric acid (7.5 mL). The resulting mixture is warmed to 100° C. (steam bath) for three minutes. The mixture is allowed to cool to room temperature. Crystallization of the crude product may begin spontaneously at this point or may be induced by addition of ether or ethyl acetate. The product 2-benzopyrylium salt H is removed by filtration and purified by recrystallization, preferably from ethanol or glacial acetic acid/ethyl acetate.

A similar synthetic sequence for preparation of 2,3-benzodiazepines is disclosed in U.S. Pat. No. 3,736,315, the entire disclosure of which is incorporated herein by reference. Synthetic strategies for preparation of 2,3-benzodiazepines are also disclosed in Horvath et al., *Progress in Neurobiology* 60(2000) p309–342 and references cited therein; the entire disclosures of which are incorporated herein by reference.

Alternative methods for preparation of intermediate H start with an aryl acetonide or indanone starting material. See Kunnetsov, E. V., and Dorofeenko, G. N., *Zh. Org. Khim.*, 6, 578–581. and M. Vajda, *Acta Chem. Acad. Sci. Hung.*, 40, p.295–307, 1964, respectively, the entire disclosures of which are incorporated herein by reference.

To synthesize a 2,3-benzodiazepine derivative of formula I having an amine substituent, the starting aromatic amine components must be protected with a protecting group or otherwise rendered unreactive in order for the amine to be rendered stable to the reaction conditions employed in the reaction schemes shown or referenced above. A means of circumventing the need for a protecting group may be to use a starting material containing an aromatic nitro group(s) in place of the desired aromatic amino group(s). The nitro group performs the same function as an amine protecting group in this synthesis and it may, following the synthesis steps that are incompatible with an amine substituent, be then reduced to an amine. Reduction of the aromatic nitro group can be done, for example, via catalytic hydrogenation. Catalytic hydrogenation provides the capability to selectively reduce the aromatic nitro group without reducing the olefin or other functionality in the intermediate. This synthetic strategy is disclosed in U.S. Pat. No. 4,614,740, wherein racemic 2,3-benzodiazepines were prepared with amino groups at a position corresponding the $R^3$ of formula I of the present invention. The entire disclosure of U.S. Pat. No. 4,614,740 is incorporated herein by reference.

Resolution of (R)-2,3-Benzodiazepines of Formula I

The synthetic procedures shown (or referenced) above produce racemic mixtures of 2,3-benzodiazepines. In order to prepare (R)-2,3-benzodiazepines of formula I that are useful in methods of the present invention, the racemic mixture must be resolved.

Racemic 2,3-benzodiazepines may, for example, be converted to the (S)-dibenzoyltartaric acid salt, which is a diastereomeric mixture of SS and RS configurations. The pair of diastereomers (R,S) and (S,S) possess different properties, e.g., differential solubilities, that allow for the use of conventional separation methods. Fractional crystallization of diastereomeric salts from a suitable solvent is one such separation method. This resolution has been successfully applied to the resolution of racemic tofisopam. See Hungarian Patent 178516 and also Toth et al., *J.Heterocyclic Chem.*, 20:09–713 (1983), the entire disclosures of which are incorporated herein by reference.

Alternatively, racemic-2,3-benzodiazepines may be derivatized via, for example, acylation of an aryl hydroxy moiety, with a chiral acylating reagent, e.g., (S)-mandelic acid. The resulting ester, has a second chiral center, and thus exists as a diastereomeric pair separable using conventional methods such as crystallization or chromatography. Following the separation, the chiral moiety with which the racemic 2,3-benzodiazepine is derivatized, may be removed.

Racemic 2,3-benzodiazepines may be separated without diastereomer formation by differential absorption on a chiral stationary phase of a chromatography column, particularly a preparative HPLC column. Chiral HPLC columns are commercially available with a variety of packing materials to suit a broad range of separation applications. Exemplary stationary phases suitable for resolving the racemic 2,3-benzodiazepines include:

(i) macrocyclic glycopeptides, such as silica-bonded vancomycin which contains 18 chiral centers surrounding three pockets or cavities;

(ii) chiral $\alpha_1$-acid glycoprotein;

(iii) human serum albumin; and (iv) cellobiohydrolase (CBH).

Chiral $\alpha_1$-acid glycoprotein is a highly stable protein immobilized onto spherical silica particles that tolerates high concentrations of organic solvents, high and low pH, and high temperatures. Human serum albumin, though especially suited for the resolution of weak and strong acids, zwitterionic and nonprotolytic compounds, has been used to resolve basic compounds. CBH is a very stable enzyme which has been immobilized onto spherical silica particles and is preferentially used for the separation of enantiomers of basic drugs from many compound classes.

The resolution of tofisopam by chiral chromatography using macrocyclic glycopeptide as a stationary phase on a Chirobiotic V™ column (ASTEAC, Whippany, N.J.) is disclosed in U.S. Pat. No. 6,080,736. Fitos et al. (*J. Chromatogr.*, 709 265 (1995)), discloses another method for resolving racemic tofisopam by chiral chromatography using a chiral $\alpha_1$-acid glycoprotein as a stationary phase on a CHIRAL-AGP™ column (ChromTech, Cheshire, UK). The latter method separates the (R)- and (S)-enantiomers and also resolves the two conformers (discussed below) of each enantiomer. These chromatographic methods, may be used generally to separate racemic 2,3-benzodiazepines into individual (R)- and (S)-enantiomers. The Chirobiotic V™ column is available in a semi-preparative size as employed for the above separation 500 mm×10 mm). The stationary phase of the Chirobiotic V™ column is commercially available in bulk for packing of preparative chromatography columns with larger sample capacity.

(R)- and (S)-enantiomers of 2,3-benzodiazepines may also exist in two stable conformations that may be assumed by the benzodiazepine ring, as generally depicted below:

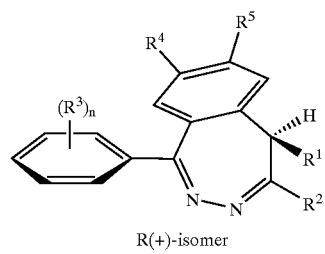

R(+)-isomer

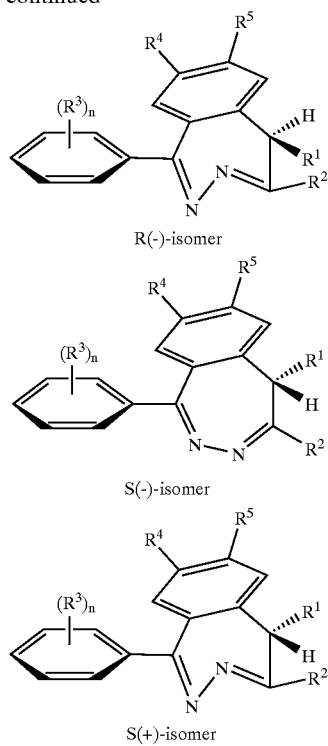

R(-)-isomer

S(-)-isomer

S(+)-isomer

The present invention includes methods as described herein that use any and all observable conformations of compounds of formula I (of the (R)-absolute configuration at carbon 5 of the benzodiazepine ring) which are biologically active in treatments to raise neutrophil levels.

Differential binding of the (+) and (−) conformers of 2,3-benzodiazepines generally, has been reported for tofisopam in binding studies with human albumin (Simongi et al. *Biochem. Pharm.*, 32(12), 1917–1920, 1983). The (+) and (−) conformers of tofisopam have also been reported as existing in an equilibrium (Zsila et al., *Journal of Liquid Chromatography & Related Technologies*, 22(5), 713–719, 1999; and references therein).

It will be understood that compounds of formula I useful in the methods of the present invention may contain one or more chiral centers in addition to chiral center at the 5-position of the benzodiazepine ring of compounds of formula I. Such compounds may exist in, and may be isolated as pure enantiomeric or diastereomeric forms or as racemic mixtures. The present invention therefore includes methods that use any possible enantiomers, diastereomers, racemates or mixtures thereof of formula I (dictated by a chiral center other than the 5-position of the benzodiazepine ring) which are biologically active in the treatment or prevention of inflammatory disease states mediated by $LTB_4$.

The compounds used in the methods of the present invention may take the form of pharmaceutically-acceptable salts. The term "salts", embraces salts commonly used to form alkali metal salts and to form addition salts of free acids or free bases. The term "pharmaceutically-acceptable salt" refers to salts that possess toxicity profiles within a range so as to have utility in pharmaceutical applications. Pharmaceutically unacceptable salts may nonetheless possess properties such as high crystallinity, which have utility in the practice of the present invention, such as for example utility in a synthetic process or in the process of resolving enantiomers from a racemic mixture. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, flumaric, pyruvic, aspartic, glutamic, benzoic, anthranilic, mesylic, salicyclic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid.

Suitable pharmaceutically acceptable base addition salts of compounds of formula I useful in methods of the invention include for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds useful in methods of the invention may be administered to individuals (mammals, including animals and humans) afflicted with $LTB_4$-mediated inflammatory disorders.

For treating or preventing inflammatory disorders mediated by $LTB_4$, the specific dose of compound according to the invention to obtain therapeutic benefit will, of course, be determined by the particular circumstances of the individual patient including, the size, weight, age and sex of the patient. Also determinative will be the nature and stage of the disease and the route of administration. For example, a daily dosage of from about 100 to 1500 mg/day may be utilized. Preferably, a daily dosage of from about 100 to 1000 mg/day may be utilized. More preferably, a daily dosage of from about 100 to 500 mg/day may be utilized. Higher or lower doses are also contemplated.

For prophylactic administration, the compounds useful in the practice of methods of the invention should be administered far enough in advance of a known event that increases the chance of an inflammatory disorder mediated by $LTB_4$, such that the compound is able to reach the site of action in sufficient concentration to exert a $LTB_4$ antagonist effect. The pharmacokinetics of specific compounds may be determined by means known in the art and tissue levels of a compound in a particular individual may be determined by conventional analyses.

One or more compounds useful in the practice of the present inventions may be administered simultaneously, or different (R)-2,3-benzodiazepines useful in the practice of the present invention may be administered at different times during treatment or prevention therapy.

The methods of the present invention may comprise administering (R)-2,3-benzodiazepines in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The compounds useful in methods of the invention may be administered for therapeutic effect by any route, for example enteral (e.g., oral, rectal, intranasal, etc.) and parenteral administration. Parenteral administration includes, for example, intravenous, intramuscular, intraarterial, intraperitoneal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For antiinflammatory use, the drug may be localized in a depot for controlled release to the circulation, or controlled release to a local site of inflammation.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions of the present invention can also be formulated so as to provide slow or controlled-release of the active ingredient therein. In general, a controlled-release preparation is a composition capable of releasing the active ingredient at the required rate to maintain constant pharmacological activity for a desirable period of time. Such dosage forms can provide a supply of a drug to the body during a predetermined period of time and thus maintain drug levels in the therapeutic range for longer periods of time than other non-controlled formulations.

For example, U.S. Pat. No. 5,674,533 discloses controlled-release compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 discloses a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 discloses controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. The patents cited above are incorporated herein by reference.

Biodegradable microparticles can be used in the controlled-release formulations of this invention. For example, U.S. Pat. No. 5,354,566 discloses a controlled-release powder that contains the active ingredient. U.S. Pat. No. 5,733,566 describes the use of polymeric microparticles that release antiparasitic compositions. These patents are incorporated herein by reference.

The controlled-release of the active ingredient can be stimulated by various inducers, for example pH, temperature, enzymes, water, or other physiological conditions or compounds. Various mechanisms of drug release exist. For example, in one embodiment, the controlled-release component can swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient (e.g., (R)-tofisopam or a pharmaceutically-acceptable salt thereof) in the pharmaceutical composition. In another embodiment, the controlled-release component is biodegradable, induced by exposure to the aqueous environment, pH, temperature, or enzymes in the body. In another embodiment, sol-gels can be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

The practice of the invention is illustrated by the following non-limiting examples.

EXAMPLES

Example 1

Synthesis of (R)-1-(3,4-dimethoxyphenyl)-4-methyl-5-ethyl-7-hydroxy-8-methoxy-5H-2,3-benzodiazepine A. Synthesis of racemic 1-(3,4-dimethoxyphenyl)-4-methyl-5-ethyl-7-hydroxy-8-methoxy-5H-2,3-benzodiazepine:

4.41 g (10 mmol) of 1-(3,4-dimethoxyphenyl)-3-methyl-4-ethyl-6,7-dimethoxyisobenzopyrilium chloride hydrochloride is dissolved in methanol (35 mL) at a temperature of 40° C. After cooling to 20–25° C., hydrazine hydrate (0.75 g, 15 mmol, dissolved in 5 mL methanol) is added. The reaction is monitored by HPLC and when complete, is evaporated to dryness. The residue is triturated with cold water (3 mL), filtered and dried to yield the crude (R,S)-1-(3,4-dimethoxyphenyl)-4-methyl-5-ethyl-7-hydroxy-8-methoxy-5H-2,3-benzo-diazepine which is subsequently triturated with hot ethyl acetate to yield the pure product.

B. Resolution of the racemate to produce (R)-1-(3,4-dimethoxyphenyl)-4-methyl-5-ethyl-7-hydroxy-8-methoxy-5H-2,3-benzodiazepine:

(R,S)-1-(3,4-Dimethoxyphenyl)-4-methyl-5-ethyl-7-hydroxy-8-methoxy-5H-2,3-benzodiazepine (43 mg, dissolved in acetonitrile) is injected onto a Chirobiotic V column (ASTEAC, whippany, N.J.) Elution of the racemate with methyl-tert-butyl ether/acetonitrile 90/10 (v/v), at 40 mL/minute, is monitored at 310 nm, 2 mm path.

The R(+) enantiomer is the first compound to elute, and is collected and dried. The R(−), S(+), S(−) enantiomers, and some residual R(+) enantiomer coelute and are collected in subsequent fractions. Approximately 20% of the R(+) isomer is converted to the R(−) isomer if left in the eluent for 24 hours. A stable 80/20 equilibrium (R(+) to R(−)) is observed between the conformers in the eluent solution.

Example 2

Synthesis of racemic-1-(3-hydroxy-4-methoxyphenyl)-4-methyl-5-ethyl-7,8-dimethoxy-5H-2,3-benzodiazepine Racemic-1-(3-hydroxy-4-methoxyphenyl)-4-methyl-5-ethyl-7,8-dimethoxy-5H-2,3-benzodiazepine was synthesized according to the route of Scheme 3.

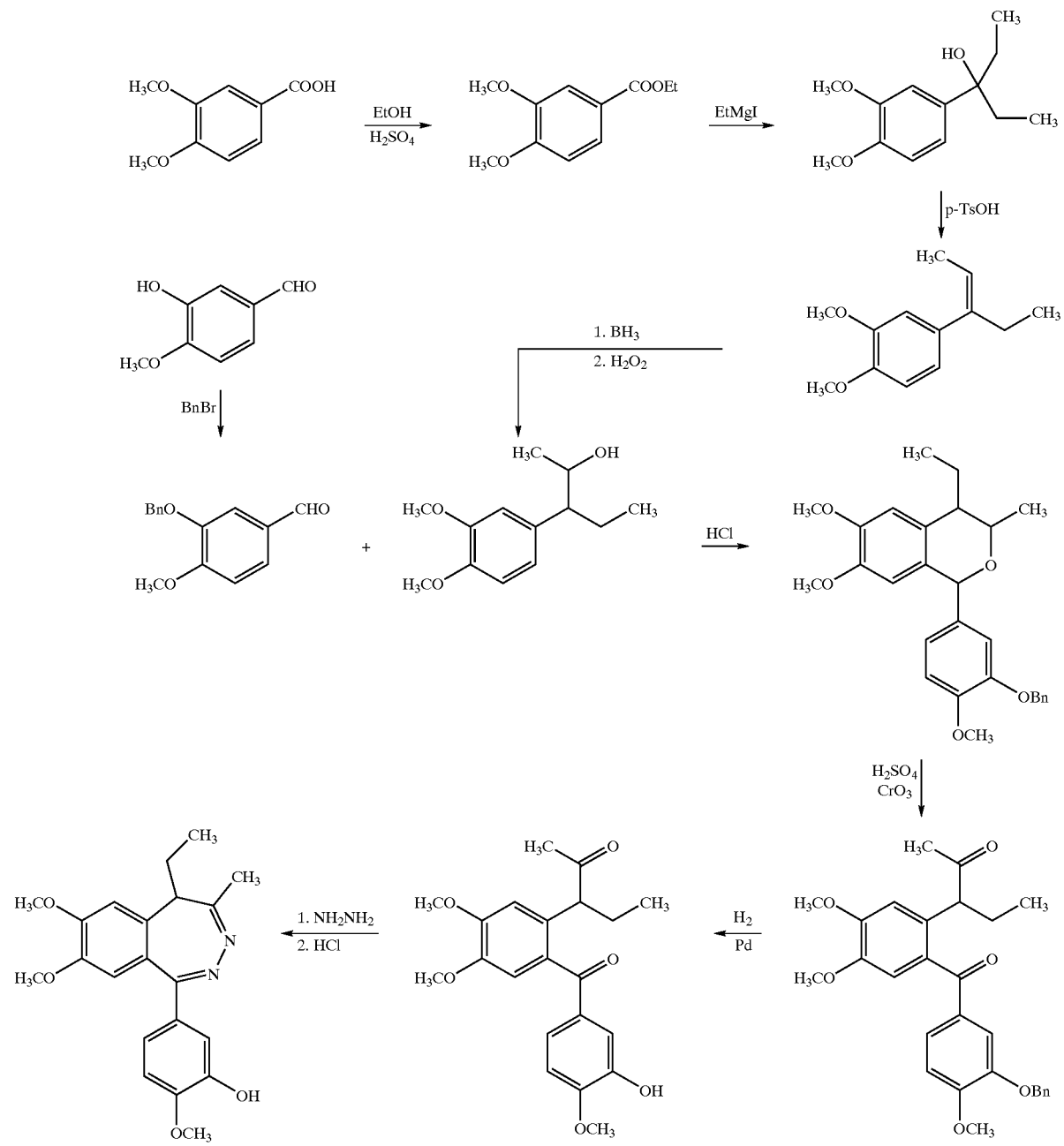

Scheme 3

A. Esterification of 3,4-dimethoxybenzoic acid to yield ethyl-3,4-dimethoxybenzoate([3943-77-9]).

A solution of 200 g of 3,4-dimethoxybenzoic acid and 35 g of concentrated sulfuric acid in 600 mL of absolute ethanol was heated at reflux overnight. The mixture was concentrated and the residue poured into water. Methylene chloride was added and the solution washed successively with water, dilute sodium bicarbonate and water, then dried and concentrated. The residue was recrystallized from acetone/hexane.

B. Addition of ethyl magnesium iodide to ethyl-3,4-dimethoxybenzoate acid to yield 3-(3,4-dimethoxyphenyl)pentan-3-ol.

A solution of 4.8 mL of iodoethane in 20 mL of ether was added dropwise to a suspension of 1.5 g of magnesium turnings in 10 mL of ether. After 5 mL of the iodoethane solution had been added, a few grains of iodine were added and the mixture was heated to induce formation of the Grignard reagent. The remaining iodoethane solution was then added. After the Grignard formation was complete, a solution of 5 g of ethyl 3,4-dimethoxybenzoate in ether was added and the mixture was allowed to stir at room temperature overnight. The reaction was quenched by addition of saturated ammonium chloride. The mixture was extracted with ether. The combined ether extracts were dried and concentrated to an oily residue. Yield: 5 g.

C. Elimination of $H_2O$ from 3-(3,4-dimethoxyphenyl)pentan-3-ol to yield 4-((1Z)-1-ethylprop-1-enyl)-1,2-dimethoxybenzene.

A solution of 5 g of crude 3-(3,4-dimethoxyphenyl)pentan-3-ol and 0.25 g of p-tolenesulfonic acid in 80 mL of benzene was heated at reflux for 1 hr with azeotropic removal of water. The mixture was then filtered through a pad of sodium bicarbonate and the filtrate concentrated. The residue was purified by distillation under reduced pressure. Yield: 2.9 g.

D. Addition of $H_2O$ to 4-((1Z)-1-ethylprop-1-enyl)-1,2-dimethoxybenzene to yield 3-(3,4-dimethoxyphenyl)pentan-2-ol.

To a solution of 26 g of 4-((1Z)-1-ethylprop-1-enyl)-1,2-dimethoxybenzene in tetrahydrofuran at 0° C. was added 189 mL of a 1.0M solution of borane-tetrahydrofuram complex in tetrahydrofuran. The mixture was stirred for 3 hr at 0° C., then 35.6 mL of 50% hydrogen peroxide was added, with simultaneous addition of SM sodium hydroxide to maintain the mixture at pH 8. The mixture was extracted with ether. The combined ether extracts were dried and concentrated.

E. Benzylation of 3-hydroxy-4-methoxybenzaldehyde to yield 4-methoxy-3-(phenylmethoxy)benzaldehyde([6346-05-0]).

A solution of 100 g of 3-hydroxy-4-methoxybenzaldehyde and 135 g of benzyl bromide in 500 mL of acetone containing a suspension of 137 g of potassium carbonate was heated at reflux overnight. The mixture was filtered, the filtrate concentrated and the residue recrystallized from toluene/hexane. Yield: 65 g.

F. Reaction of 3-(3,4-dimethoxyphenyl)pentan-2-ol with 4-methoxy-3-(phenyl-methoxy)benzaldehyde to yield 4-(4-ethyl-6,7-dimethoxy-3-methyliso-chromanyl)-1-methoxy-2-(phenylmethoxy)benzene.

A solution of 14 g of 4-methoxy-3-(phenylmethoxy) benzaldehyde and 15 g of 3-(3,4-dimethoxyphenyl)pentan-2-ol in 0.3 L of dioxane was saturated with hydrogen chloride gas. The mixture was heated at reflux for 3 hr, saturated again with hydrogen chloride gas and allowed to stir at room temperature overnight. It was then poured into water, basified with dilute sodium hydroxide and extracted with methylene chloride. The combined methylene chloride extracts were dried and concentrated.

G. Ring-opening of 4-(4-ethyl-6,7-dimethoxy-3-methyliso-chromanyl)-1-methoxy-2-(phenylmethoxy)benzene to yield 3-(4,5-dimethoxy-2-{[4-methoxy-3-(phenylmethoxy)phenyl]carbonyl}phenyl)pentan-2-one.

To a solution of 30 g of crude 4-(4-ethyl-6,7-dimethoxy-3-methyliso-chromanyl)-1-methoxy-2-(phenylmethoxy) benzene in 450 mL of acetone at 5° C. was added a solution of 30 g of chromic oxide in 300 mL of 35% sulfuric acid. The mixture was stirred at room temperature for 2 hr, neutralized by adding cold 10% sodium hydroxide and concentrated to remove acetone. Then, water was added and the mixture was extracted with methylene chloride. The combined methylene chloride extracts were dried and concentrated. The residue was purified by column chromatography on silica gel. Yield: 10 g H. Debenzylation of 3-(4,5-dimethoxy-2-{[4-methoxy-3-(phenylmethoxy)-phenyl]carbonyl}phenyl)pentan-2-one to yield 3-{2-[(3-hydroxy-4-methoxy-phenyl)carbonyl]-4,5-dimethoxyphenyl}pentan-2-one.

A solution of 10 g of 3-(4,5-dimethoxy-2-{[4-methoxy-3-(phenylmethoxy)-phenyl]carbonyl}phenyl)pentan-2-one in methylene chloride containing a suspension of 0.9 g of 10% palladium on carbon was hydrogenated at 80 psi for 1 hr. The mixture was filtered through diatomaceous earth and the filtrate concentrated. Yield: 6.5 g I. Annulation of 3-{2-[(3-hydroxy-4-methoxyphenyl)carbonyl]-4,5-dimethoxyphenyl}pentan-2-one by reaction with hydrazine to yield 1-(3-hydroxy-4-methoxyphenyl)-4-methyl-5-ethyl-7,8-dimethoxy-5H-2,3-benzodiazepine.

A solution of 6.5 g of 3-{2-[(3-hydroxy-4-methoxyphenyl)carbonyl]-4,5-dimethoxyphenyl}pentan-2-one and 2.2 mL of hydrazine in 130 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 0.97g The product 1-(3-hydroxy-4-methoxyphenyl)-4-methyl-5-ethyl-7,8-dimethoxy-5H-2,3-benzodiazepine was analyzed by HPLC, elemental analysis, GC/MS, proton NMR and differential scanning calorimetry (DSC). The data are as follows:

Purity: 99.29% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

DSC: Temperature program 100° C. to 300° C. at 5° C./min, indicated molar purity=99.75% and melting point of 158.6° C.

Elemental analysis (calculated/analysis): % C—68.09/68.08; % H—6.61/6.57; N—7.53/7.35. Calculated values include 0.02 equivalents of ethyl acetate and 0.09 equivalents of residual water.

NMR (DCCl₃) (performed on GE QE 300): 1.08ppm (t, 3H); 1.99 (s, 3H); 2.11 (m, 2H); 2.75 (m, 1H); 3.75 (s, 3H); 3.93 (s, 3H); 3.97 (s, 3H); 6.46 (bs, 1H); 6.72 (s, 1H); 6.86 (m, 2H); 7.18 (d, 1H); 7.48 (s, 1H).

Example 3

Synthesis of 1-(3,4-dimethoxyphenyl)-4-methyl-5-ethyl-7-methoxy-8-hydroxy-5H-2,3-benzodiazepine Racemic 1-(3,4-dimethoxyphenyl)-4-methyl-5-ethyl-7-methoxy-8-hydroxy-5H-2,3-benzodiazepine was synthesized according to the route of Scheme 4.

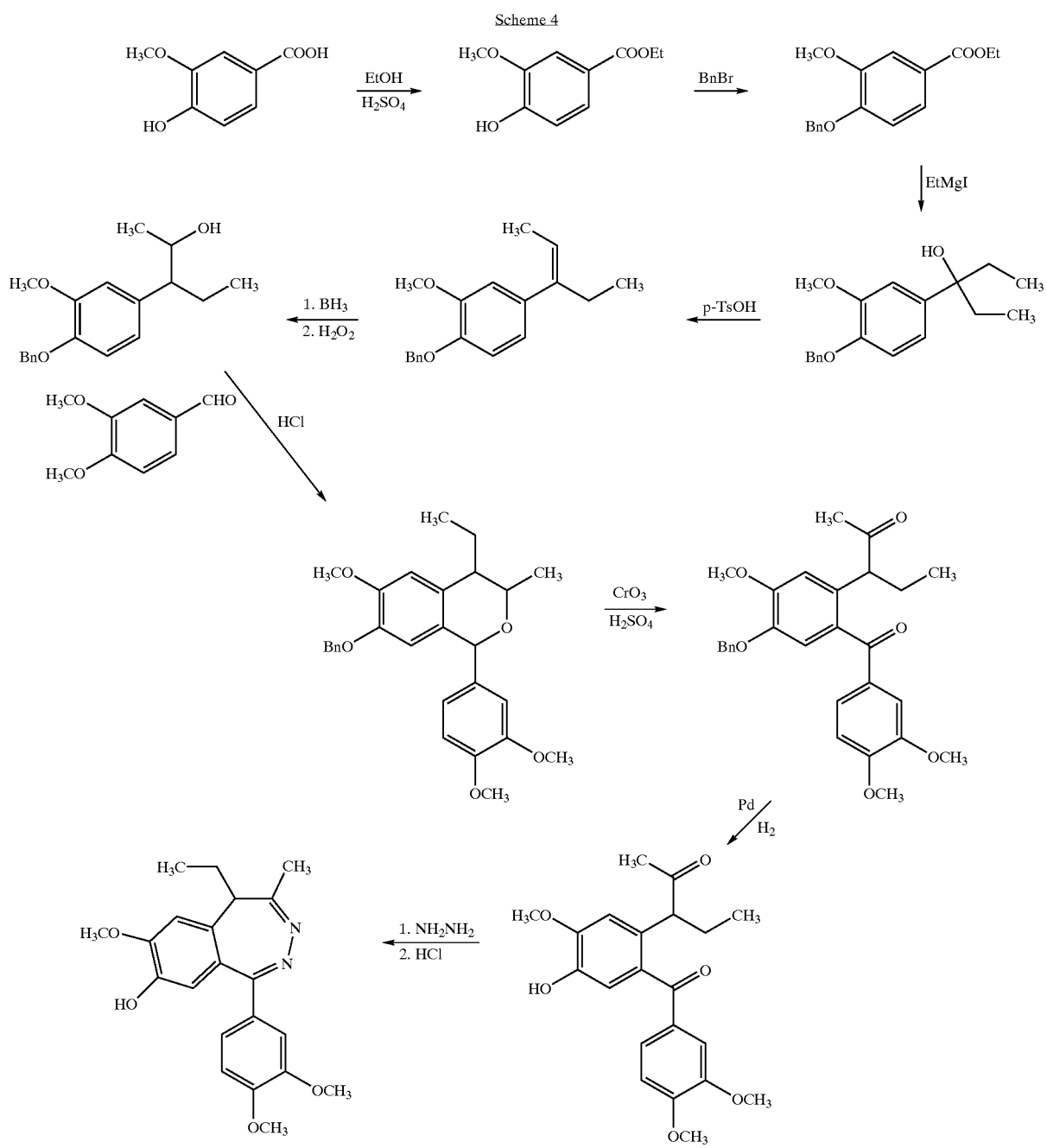

Scheme 4

A. Esterification of 3-methoxy-4-hydroxybenzoic acid to yield ethyl-3-methoxy-4-hydroxybenzoate.

A solution of 100 g of 3-methoxy-4-hydroxybenzoic acid and 17 g of concentrated sulfuric acid in 300 mL of absolute ethanol was heated at reflux overnight. The mixture was concentrated and the residue poured into water. Methylene chloride was added and the solution washed successively with water, dilute sodium bicarbonate and water, then dried and concentrated. Yield: 118 g B. Benzylation of ethyl-3-methoxy-4-hydroxybenzoate to yield ethyl-3-methoxy-4-benzyloxybenzoate.

A solution of 118 g of ethyl-3-methoxy-4-hydroxybenzoate and 86 mL of benzyl bromide in 600 mL of acetone containing a suspension of 124 g of potassium carbonate was heated at reflux overnight. The mixture was filtered, the filtrate concentrated and the residue recrystallized from acetone.

C. Addition of ethyl magnesium iodide to ethyl-3-methoxy-4-benzyloxybenzoate to yield 3-(3-methoxy-4-benzyloxyphenyl)pentan-3-ol.

Iodoethane (112 mL) was added dropwise to a suspension of 35 g of magnesium turnings in 160 mL of ether. After the formation of ethyl magnesium iodide was complete, a solution of 142 g of ethyl 3-methoxy-4-benzyloxybenzoate in ether was added and the mixture was allowed to stir at room temperature for 3 days. The reaction was quenched by addition of saturated ammonium chloride. The layers were separated and the ether layer was dried and concentrated to an oily residue. Yield: 110 g.

D. Elimination of H₂O from 3-(3-methoxy-4-benzyloxyphenyl)pentan-3-ol to yield 4-((1Z)-1-ethylprop-1-enyl)-1-benzyloxy-2-methoxybenzene.

A solution of 110 g of crude 3-(3-methoxy-4-benzyloxyphenyl)pentan-3-ol and 7 g of p-tolenesulfonic acid in 2 L of benzene was heated at reflux for 4 hr with azeotropic removal of water. The mixture was then filtered through a pad of sodium bicarbonate and the filtrate concentrated. The residue was purified by column chromatography on neutral alumina.

E. Addition of H₂O to 4-((1Z)-1-ethylprop-1-enyl)-1-benzyloxy-2-methoxybenzene to yield 3-(3-methoxy-4-benzyloxyphenyl)pentan-2-ol.

To a solution of 96 g of 4-((1Z)-1-ethylprop-1-enyl)-1-benzyloxy-2-methoxybenzene in tetrahydrofuran at 0° C. was added 510 mL of a 1.0M solution of borane-tetrahydrofuran complex in tetrahydrofuran. The mixture was stirred for 3 hr at 0° C., then 204 mL of 25% hydrogen peroxide was added. The mixture was adjusted to pH 8 by addition of 5M sodium hydroxide and extracted with ether. The combined ether extracts were dried and concentrated. Yield: 102 g.

F. Reaction of 3-(3-methoxy-4-benzyloxyphenyl)pentan-2-ol with 3,4-dimethoxybenzaldehyde to yield 4-(4-ethyl-6-methoxy-7-benzyloxy-3-methyliso-chromanyl)-1,2-dimethoxybenzene.

A solution of 46 g of 3,4-dimethoxybenzaldehyde and 100 g of crude 3-(3-methoxy-4-benzyloxyphenyl)pentan-2-ol in 0.3 L of dioxane was saturated with hydrogen chloride gas. The mixture was heated at reflux for 3 hr, then poured into water, basified with dilute sodium hydroxide and extracted with methylene chloride. The combined methylene chloride extracts were dried and concentrated.

G. Ring-opening of 4-(4-ethyl-6-methoxy-7-benzyloxy-3-methyliso-chromanyl)-1,2-dimethoxybenzene to yield 3-(4-benzyloxy-5-methoxy-2-{[3,4-dimethoxyphenyl]carbonyl}phenyl)pentan-2-one.

To a solution of 50 g of crude 4-(4-ethyl-6-methoxy-7-benzyloxy-3-methyliso-chromanyl)-1,2-dimethoxybenzene in acetone at 5° C. was added a solution of 50 g of chromic oxide in 500 mL of 35% sulfuric acid. The mixture was stirred at room temperature for 2 hr, neutralized by adding cold 10% sodium hydroxide and concentrated to remove acetone. Water was added and the mixture extracted with methylene chloride. The combined methylene chloride extracts were dried and concentrated. The residue was purified by column chromatography on silica gel. Yield: 18 g H. Debenzylation of 3-(4-benzyloxy-5-methoxy-2-{[3,4-dimethoxy-phenyl]carbonyl}phenyl)pentan-2-one to yield 3-{2-[(3,4-dimethoxy-phenyl)carbonyl]-4-hydroxy-5-methoxyphenyl}pentan-2-one.

A solution of 18 g of 3-(4-benzyloxy-5-methoxy-2-{[3,4-dimethoxy-phenyl]carbonyl}phenyl)pentan-2-one in methylene chloride containing a suspension of 2 g of 10% palladium on carbon was hydrogenated at 80 psi for 1 hr. The mixture was filtered through diatomaceous earth and the filtrate concentrated. Yield: 15 g I. Annulation of 3-{2-[(3,4-dimethoxy-phenyl)carbonyl]-4-hydroxy-5-methoxyphenyl}pentan-2-one by reaction with hydrazine to yield 1-(3,4-dimethoxyphenyl)-4-methyl-5-ethyl-7-methoxy-8-hydroxy-5H-2,3-benzodiazepine.

A solution of 14 g of 3-{2-[(3,4-dimethoxy-phenyl)carbonyl]-4-hydroxy-5-methoxyphenyl}pentan-2-one and 4.7 mL of hydrazine in 280 mL of ethanol was heated at reflux for 0.5 hr. After allowing the solution to cool to room temperature, it was saturated with HCl gas. The mixture was then concentrated to a volume of about 5 mL, basified with concentrated ammonium hydroxide, and extracted with methylene chloride. The combined methylene chloride extracts were dried and concentrated, and the residue recrystallized from ethyl acetate/hexane. Yield: 1.5 g The product 1-(3,4-dimethoxyphenyl)-4-methyl-5-ethyl-7-methoxy-8-hydroxy-5H-2,3-benzodiazepine was analyzed by HPLC, elemental analysis, GC/MS, proton NMR and differential scanning calorimetry (DSC). The data are as follows:

Purity: 98.36% by HPLC (% area). Column: Betasil Phenyl 4.6×150 mm. Mobile Phase: Acetonitrile::0.01M Phosphate Buffer (70::30). Flow Rate: 0.5 mL/min. Wavelength: 254 nm.

GC-MS; M/e=358; with the fragmentation pattern matching the proposed structure.

Differential scanning calorimetry (DSC): Temperature program 100° C. to 300° C. at 5° C./min, indicated molar purity=99.14% and melting point of 146.2° C.

Elemental analysis (calculated/analysis): % C—68.14/68.12; % H—6.63/6.63; N—7.43/7.20. The calculated values include 0.1M of residual ethyl acetate.

NMR (DCCl₃) (performed on GE QE 300): 1.08 ppm (t, 3H); 1.96 (s, 3H); 2.10 (m, 2H); 2.77 (m, 1H); 3.91 (s, 3H); 3.93 (s, 3H); 3.98 (s, 3H); 5.73 (bs, 1H); 6.70 (s, 1H); 6.80 (d, 1H); 6.95 (s, 1H); 7.00 (d, 1H); 7.58 (s, 1H).

Example 4

Resolution of 1-(3-hydroxy-4-methoxyphenyl)-4-methyl-5-ethyl-7,8-dimethoxy-5H-2,3-benzodiazepine The enantiomers of racemic-1-(3-hydroxy-4-methoxyphenyl)-4-methyl-5-ethyl-7,8-dimethoxy-5H-2,3-benzodiazepine are resolved by chiral chromatography as follows.

Racemic-1-(3-hydroxy-4-methoxyphenyl)-4-methyl-5-ethyl-7,8-dimethoxy-5H-2,3-benzodiazepine is loaded onto a semipreparative (500 mm×10 mm) Chirobiotic V column (ASTEC, Whippany, N.J.). Elution of the enantiomeric mixture with methyl-tert-butyl ether/acetonitrile (90/10 V/V), at a flow rate of 40 mL/min, is monitored at 310 nm. Fraction size is 10–20 mL and fractions are subjected to analytical chromatography using the same solvent composition on an analytical (150×4.6 mm) Chirobiotic V column. The fractions containing each isolated enantiomer are processed by removing the elution solvent in vacuo.

Example 5

LTB₄ Binding Assay

The LTB₄ receptor binding activity of racemic tofisopam and enantiomerically pure (R)- and (S)-tofisopam was determined via the guinea pig spleen membrane assay of Cheng et al., *J. Pharmacol. Exp. Ther.*, 236(1), 126–132, 1986.

Figure 2:
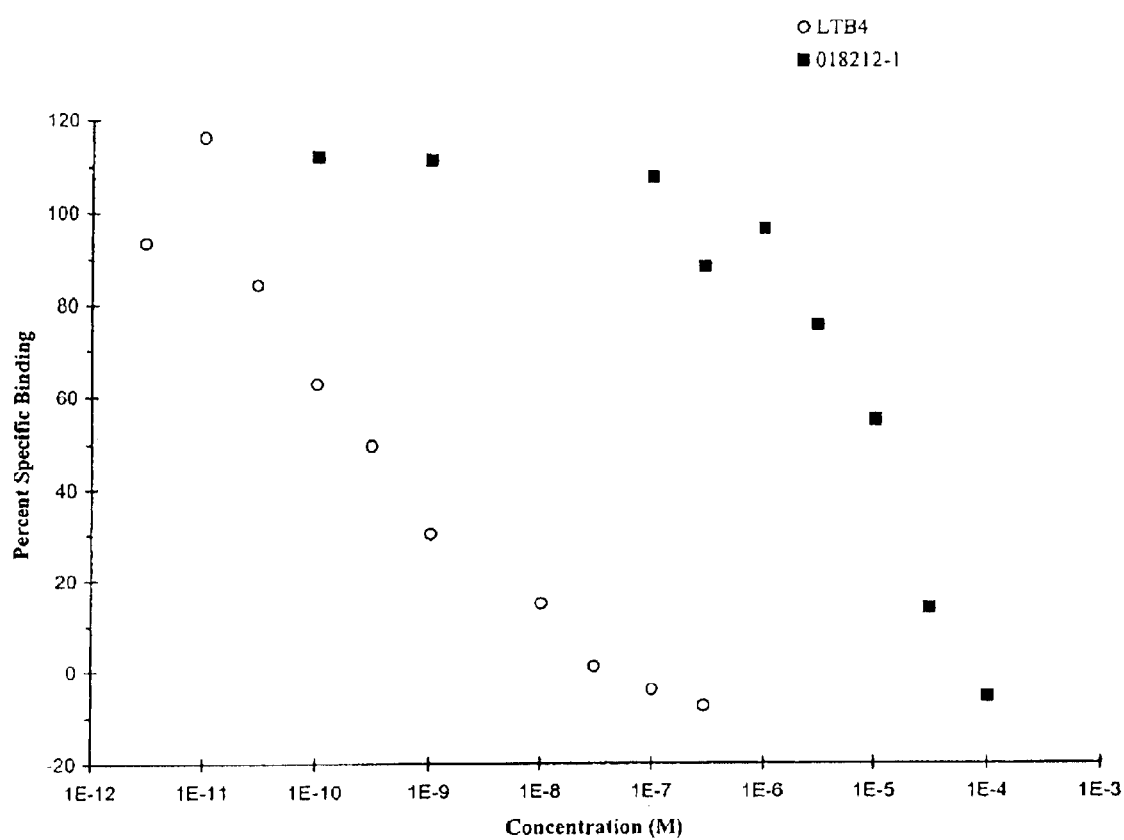
FIG. 2 is a plot of data gathered in a competitive binding study of the displacement of [$^3$H]LTB$_4$ by racemic tofisopam from LTB$_4$ receptors. IC$_{50}$ and K$_i$ values for racemic tofisopam displacement of [$^3$H]LTB$_4$ were generated.
Figure 3:
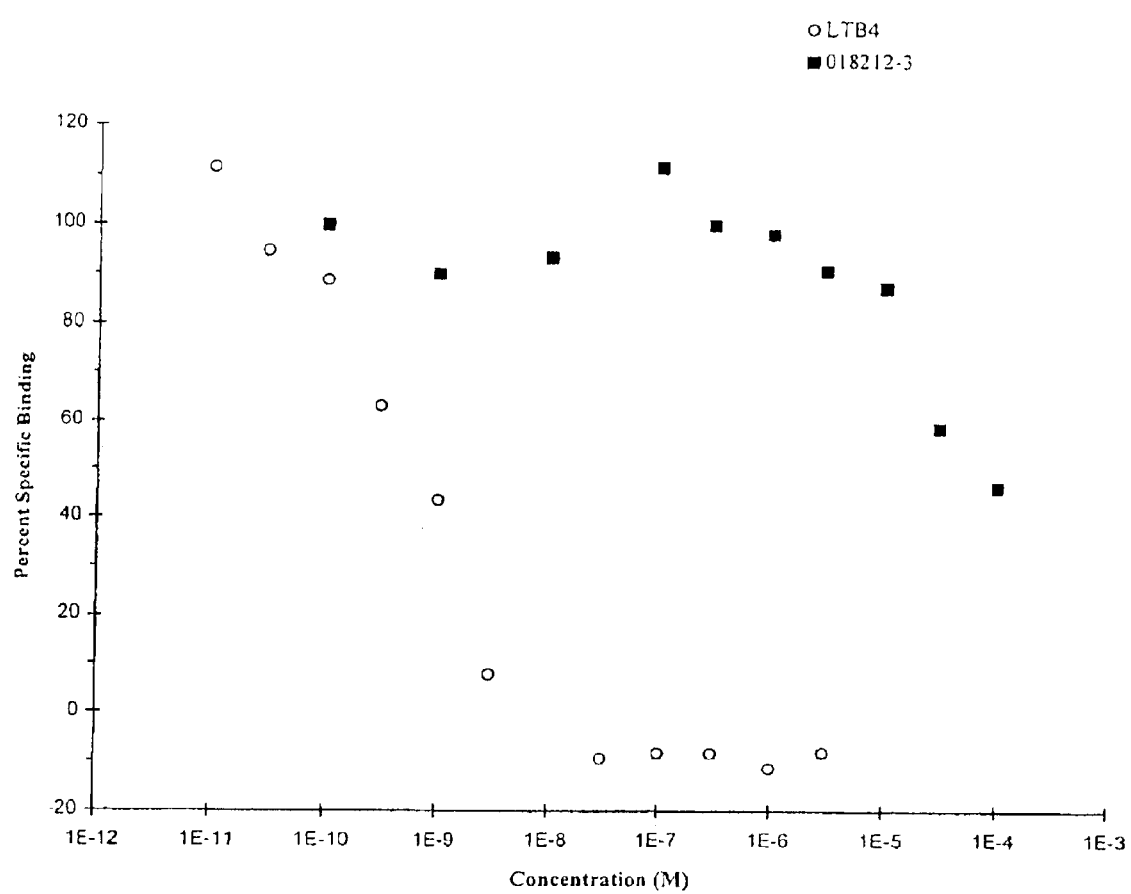
FIG. 3 is a plot of data gathered in a competitive binding study of the displacement of [$^3$H]LTB$_4$ by (S)-tofisopam from LTB$_4$ receptors. IC$_{50}$ and K$_i$ values for (S)-tofisopam displacement of [$^3$H]LTB$_4$ were generated.

Reactions were carried out in a phosphate buffer (pH 7.4) containing NaCl, MgCl₂, EDTA, and bacitracin. The reaction volume of 150 μL containing 1.0 mg/mL of the Guinea pig spleen membrane preparation and 1 nM [³H]LTB₄, with or without a competitor, was incubated at 0–4° C. for 2 hours. Competitors included 2,3-benzodiazepines, and LTB₄ as a control. The reaction was terminated by rapid vacuum filtration onto glass fiber filters. The filter was washed with cold buffer, dried and placed in a scintillation vial. Radioactivity trapped onto the filters was determined and compared to control values in order to ascertain any interactions of the test compound with the $LTB_4$ binding site. Data gathered in the binding experiments for test compounds and standards are shown graphically in FIG. 1, FIG. 2 and FIG. 3, and summarized in Table 2 below.

TABLE 2

Summary of [$^3$H]$LTB_4$ binding data for (R)-, (S)- and racemic-1-(3,4-dimethoxyphenyl-4-methyl-5-ethyl-7,8-dimethoxy-5H-2,3-benzodiazepine

| Test Substance | $K_i$ ($\mu M$) |
|---|---|
| $LTB_4$ | 0.0002–0.0009 |
| (S)-1-(3,4-dimethoxyphenyl)-4-methyl-5-ethyl-7,8-dimethoxy-5H-2,3-benzodiazepine | 76.0 |
| Racemic-1-(3,4-dimethoxyphenyl)-4-methyl-5-ethyl-7,8-dimethoxy-5H-2,3-benzodiazepine | 4.52 |
| (R)-1-(3,4-dimethoxyphenyl)-4-methyl-5-ethyl-7,8-dimethoxy-5H-2,3-benzodiazepine | 0.444 |

The binding data shows that binding of racemic 1-(3,4-dimethoxy-phenyl)-4-methyl-7,8-dimethoxy-5H-2,3-benzodiazepine to the $LTB_4$ receptor is primarily due to the (R)-enantiomer, which binds with a $K_i$ greater than 150× that of the (S)-enantiomer.

Example 6

Effect of Tofisopam in a Rabbit model of $LTB_4$-Induced Dermal Inflammation

A. Test Animals and Test Compounds

Ten female New Zealand White Rabbits were assigned to dose groups as summarized in Table 3 below.

TABLE 3

Test groups for the Rabbit model of $LTB_4$-induced dermal inflammation.

| Test Group | Animal # | Test article | Dose (mg/kg, IP) |
|---|---|---|---|
| 1 | 151–152 | Vehicle | 0 |
| 2 | 251–252 | (S)-tofisopam | 60 |
| 3 | 351–352 | (R)-tofisopam | 60 |
| 4 | 451–452 | (R,S)-tofisopam | 60 |
| 5 | 551–552 | dexamethasone | 0.5 |

Test compounds were prepared as follows. The vehicle was first prepared by dissolving 100 mg of hydroxypropylmethylcellulose 2910 (HPMC)(Sigma Chemical, St. Louis, Mo.) in 50 mL of 0.9% saline to yield a concentration of 2% HPMC. The three test articles, (R)-, (S)- and racemic tofisopam, were formulated by adding 1 g of each test article to 10 mL of vehicle.

B. Dosing and Intradermal Challenge

On Day 0, the rabbits were sedated with ketamine/xylazine (35/5 mg/kg, s.c.) and an area of approximately 8×14 cm on the back was closely and carefully clipped to expose the skin, but not inflame or otherwise damage the epithelium. A grid of ten squares each approximately 2.5× 2.5 cm was drawn on each animal's back using an indelible marker. The animals were then dosed intraperitoneally with the appropriate test article corresponding to the group. Thirty minutes after dosing with test or control article, the animals were challenged intradermally with the $LTB_4$ or $LTB_4$-aminopropamide ($LTB_4$-AP, a synthetic $LTB_4$ agonist) in the appropriate site as shown in Table 4. Each injection site was marked with an indelible marker in order to identify the exact location of the intradermal injection site. Sixty minutes after challenge, the animals were treated again with tofisopam or control articles. The animals were sacrificed 4 hrs. after challenge, and the intradermal injection sites were excised, fixed in 10% neutral buffered formalin (NBF), and submitted for histopathology. H&E-stained sections were read by a board-certified veterinary pathologist using light microscopy.

TABLE 4

Intradermal injection site grid for test animals.

| | Anterior | |
|---|---|---|
| Left | 0 | 0 | Right |
| | 500 | 500 | |
| | 1000 | 1000 | |
| | 2000 | 2000 | |
| | 2000 | 2000 | |
| | Posterior | |

C. Necropsy

All animals were sacrificed 4 hr after challenge. The intradermal challenge sites were excised, placed on unique cardboard squares, fixed in 10% NBF, and submitted for histopathology. The skin sections included the epidermis and the subcutis, down to the back musculature.

D. Histopathology

The marked skin sections were fixed for at least 48 hours on small cardboard squares. At gross trimming, three levels were cut through marked skin region in order to assure that the injection sites is brought into the plane of section. The skins were gross trimmed, processed by dehydration, embedded in paraffin, sectioned at 3–5 $\mu$m, and stained with hematoxylin and eosin.

The tissues were evaluated histopathologically via light microscopy by a board-certified veterinary pathologist. Initially, the identity of the slides was masked in order to perform the initial evaluation and rank the slides. The slides were then unmasked and there was a careful assessment of the lesions and careful comparison of the tofisopam-treated sites to the vehicle and positive control tissues. The lesions were graded based upon the degree of inflammation and the degree of edema. The severity of the inflammation and edema was keyed as follows: 0=normal; T=trace; 1=minimal; 2=mild; 3=moderate; 4=marked.

E. Histopathology

The histopathology findings are summarized in Table 5 below. Both $LTB_4$ and $LTB_4$-ap produced focal skin wheals characterized by edema of the subdermis and a brisk, dose-dependent influx of neutrophils. The inflammation was composed of numerous neutrophils attached and marginated in small vessels, perivascular inflammatory cuffs, and scattered throughout the dermis. Additionally, some inflammation and edema was present in the superficial dermis. The administration of (R)-tofisopam resulted in a meaningful reduction in the severity of the inflammatory cell infiltration and less edema. There were no meaningful reduction in the inflammation and edema in the vehicle-treated, the (S)-tofisopam treated, the racemic tofisopam treated, or the dexamethasone-treated animals.

TABLE 5

Summary of histologic findings in rabbits injected intradermally with LTB$_4$ or LTB-ap and treated with (R)-, (S)-, or racemic tofisopam, vehicle or dexamethasone.

| Test animal/injection site | LT Agent | Dose (ng) | Test compound | Inflammation score | Edema score |
|---|---|---|---|---|---|
| 151/0-L | Vehicle | 0 | vehicle | T | T |
| 151/0-R | Vehicle | 0 | vehicle | 1 | 1 |
| 151/500-L | LTB$_4$ | 500 | vehicle | 1 | 1 |
| 151/500-R | LTB-ap | 500 | vehicle | 1 | 2 |
| 151/1000-L | LTB$_4$ | 1000 | vehicle | 3 | 2 |
| 151/1000-R | LTB-ap | 1000 | vehicle | 3+ | 2 |
| 151/2000-L | LTB$_4$ | 2000 | vehicle | 3 | 2 |
| 151/2000-R | LTB-ap | 2000 | vehicle | 3 | 2 |
| 151/2000-L | LTB$_4$ | 2000 | vehicle | 3 | 2 |
| 151/2000-R | LTB-ap | 2000 | vehicle | 3 | 2 |
| 152/0-L | Vehicle | 0 | vehicle | 1 | 1 |
| 152/0-R | Vehicle | 0 | vehicle | 1 | 1 |
| 152/500-L | LTB$_4$ | 500 | vehicle | 2 | 2 |
| 152/500-R | LTB-ap | 500 | vehicle | 2 | 3 |
| 152/1000-L | LTB$_4$ | 1000 | vehicle | 3 | 4 |
| 152/1000-R | LTB-ap | 1000 | vehicle | 3 | 4 |
| 152/2000-L | LTB$_4$ | 2000 | vehicle | 3 | 4 |
| 152/2000-R | LTB-ap | 2000 | vehicle | 2 | 4 |
| 152/2000-L | LTB$_4$ | 2000 | vehicle | 2 | 2 |
| 152/2000-R | LTB-ap | 2000 | vehicle | 2 | 2 |
| 251/0-L | Vehicle | 0 | (S)-tofisopam | T | T |
| 251/0-R | Vehicle | 0 | (S)-tofisopam | 1 | 1 |
| 251/500-L | LTB$_4$ | 500 | (S)-tofisopam | 1 | 2 |
| 251/500-R | LTB-ap | 500 | (S)-tofisopam | 1 | 2 |
| 251/1000-L | LTB$_4$ | 1000 | (S)-tofisopam | 1 | 3 |
| 251/1000-R | LTB-ap | 1000 | (S)-tofisopam | 1 | 3 |
| 251/2000-L | LTB$_4$ | 2000 | (S)-tofisopam | 3 | 2 |
| 251/2000-R | LTB-ap | 2000 | (S)-tofisopam | 2 | 2 |
| 251/2000-L | LTB$_4$ | 2000 | (S)-tofisopam | 2 | 2 |
| 251/2000-R | LTB-ap | 2000 | (S)-tofisopam | 2 | 1 |
| 252/0-L | Vehicle | 0 | (S)-tofisopam | 1 | 1 |
| 252/0-R | Vehicle | 0 | (S)-tofisopam | 1 | 1 |
| 252/500-L | LTB$_4$ | 500 | (S)-tofisopam | 2 | 2 |
| 252/500-R | LTB-ap | 500 | (S)-tofisopam | 3+ | 3 |
| 252/1000-L | LTB$_4$ | 1000 | (S)-tofisopam | 3+ | 4 |
| 252/1000-R | LTB-ap | 1000 | (S)-tofisopam | 3+ | 4 |
| 252/2000-L | LTB$_4$ | 2000 | (S)-tofisopam | 3+ | 4 |
| 252/2000-R | LTB-ap | 2000 | (S)-tofisopam | 3+ | 4 |
| 252/2000-L | LTB$_4$ | 2000 | (S)-tofisopam | 2 | 2 |
| 252/2000-R | LTB-ap | 2000 | (S)-tofisopam | 2 | 2 |
| 351/0-L | Vehicle | 0 | (R)-tofisopam | 0 | 0 |
| 351/0-R | Vehicle | 0 | (R)-tofisopam | 1 | 1 |
| 351/500-L | LTB$_4$ | 500 | (R)-tofisopam | 1 | 1 |
| 351/500-R | LTB-ap | 500 | (R)-tofisopam | 1 | 1 |
| 351/1000-L | LTB$_4$ | 1000 | (R)-tofisopam | 1 | 2 |
| 351/1000-R | LTB-ap | 1000 | (R)-tofisopam | 1 | 2 |
| 351/2000-L | LTB$_4$ | 2000 | (R)-tofisopam | 1–2 | 2 |
| 351/2000-R | LTB-ap | 2000 | (R)-tofisopam | 1 | 2 |
| 351/2000-L | LTB$_4$ | 2000 | (R)-tofisopam | 1 | 2 |
| 351/2000-R | LTB-ap | 2000 | (R)-tofisopam | 1 | 2 |
| 352/0-L | Vehicle | 0 | (R)-tofisopam | 1 | 2 |
| 352/0-R | Vehicle | 0 | (R)-tofisopam | 1 | 2 |
| 352/500-L | LTB$_4$ | 500 | (R)-tofisopam | 1 | 3 |
| 352/500-R | LTB-ap | 500 | (R)-tofisopam | 1 | 3 |
| 352/1000-L | LTB$_4$ | 1000 | (R)-tofisopam | 2 | 3 |
| 352/1000-R | LTB-ap | 1000 | (R)-tofisopam | 2 | 3 |
| 352/2000-L | LTB$_4$ | 2000 | (R)-tofisopam | 1 | 3 |
| 352/2000-R | LTB-ap | 2000 | (R)-tofisopam | 2 | 3 |
| 352/2000-L | LTB$_4$ | 2000 | (R)-tofisopam | 1 | 2 |
| 352/2000-R | LTB-ap | 2000 | (R)-tofisopam | 1 | 1 |
| 451/0-L | Vehicle | 0 | (R,S)-tofisopam | 1 | 2 |
| 451/0-R | Vehicle | 0 | (R,S)-tofisopam | 1 | 2 |
| 451/500-L | LTB$_4$ | 500 | (R,S)-tofisopam | 2 | 2 |
| 451/500-R | LTB-ap | 500 | (R,S)-tofisopam | 2 | 2 |
| 451/1000-L | LTB$_4$ | 1000 | (R,S)-tofisopam | 3 | 3 |
| 451/1000-R | LTB-ap | 1000 | (R,S)-tofisopam | 3 | 3 |
| 451/2000-L | LTB$_4$ | 2000 | (R,S)-tofisopam | 2 | 2 |
| 451/2000-R | LTB-ap | 2000 | (R,S)-tofisopam | 2 | 2 |
| 451/2000-L | LTB$_4$ | 2000 | (R,S)-tofisopam | 1 | 1 |
| 451/2000-R | LTB-ap | 2000 | (R,S)-tofisopam | 1 | 1 |
| 452/0-L | Vehicle | 0 | (R,S)-tofisopam | 1 | 1 |
| 452/0-R | Vehicle | 0 | (R,S)-tofisopam | 1 | 2 |
| 452/500-L | LTB$_4$ | 500 | (R,S)-tofisopam | 2 | 3 |
| 452/500-R | LTB-ap | 500 | (R,S)-tofisopam | 2 | 3 |
| 452/1000-L | LTB$_4$ | 1000 | (R,S)-tofisopam | 2 | 3 |
| 452/1000-R | LTB-ap | 1000 | (R,S)-tofisopam | 3 | 3 |
| 452/2000-L | LTB$_4$ | 2000 | (R,S)-tofisopam | 3 | 3 |
| 452/2000-R | LTB-ap | 2000 | (R,S)-tofisopam | 2 | 3 |
| 452/2000-L | LTB$_4$ | 2000 | (R,S)-tofisopam | 3 | 2 |
| 452/2000-R | LTB-ap | 2000 | (R,S)-tofisopam | 2 | 2 |
| 551/0-L | Vehicle | 0 | dexamethasone | 1 | 0 |
| 551/0-R | Vehicle | 0 | dexamethasone | 1 | 0 |
| 551/500-L | LTB$_4$ | 500 | dexamethasone | 3 | 3 |
| 551/500-R | LTB-ap | 500 | dexamethasone | 2 | 3 |
| 551/1000-L | LTB$_4$ | 1000 | dexamethasone | 3 | 3 |
| 551/1000-R | LTB-ap | 1000 | dexamethasone | 2 | 3 |
| 551/2000-L | LTB$_4$ | 2000 | dexamethasone | 2 | 3 |
| 551/2000-R | LTB-ap | 2000 | dexamethasone | 2 | 2 |
| 551/2000-L | LTB$_4$ | 2000 | dexamethasone | 1 | 1 |
| 551/2000-R | LTB-ap | 2000 | dexamethasone | 1 | 1 |
| 552/0-L | Vehicle | 0 | dexamethasone | 0 | 1 |
| 552/0-R | Vehicle | 0 | dexamethasone | 1 | 1 |
| 552/500-L | LTB$_4$ | 500 | dexamethasone | 2 | 2 |
| 552/500-R | LTB-ap | 500 | dexamethasone | 3 | 2 |
| 552/1000-L | LTB$_4$ | 1000 | dexamethasone | 3 | 2 |
| 552/1000-R | LTB-ap | 1000 | dexamethasone | 2 | 3 |
| 552/2000-L | LTB$_4$ | 2000 | dexamethasone | 1+ | 3 |
| 552/2000-R | LTB-ap | 2000 | dexamethasone | 2 | 3 |
| 552/2000-L | LTB$_4$ | 2000 | dexamethasone | 1 | 2 |
| 552/2000-R | LTB-ap | 2000 | dexamethasone | 2 | 1 |

Example 7

Dextran Sulfate Sodium Induced Colitis: Mouse Model of Inflammatory Bowel Disease In this model of colitis, an acute inflammation of the colon was produced by administration of dextran sulfate sodium (DSS) as a 5% solution in tap water. This colitis was characterized by histological events and an influx of neutrophils, macrophages and mediators of inflammation similar to those observed with human inflammatory bowel diseases. Several drugs known to be of useful for treating IBD, such as corticosteroids and 5-ASA, have been shown to have activity in this model. The following study was conducted in accordance with protocols of Okayasu et al., *Gastroenterology*, 98:694–702, 1990.

One hundred ten test animals (female, 6 week old Swiss Webster mice, 18–30 g) were divided into ten groups, selected to eliminate any statistical differences in mean group weight.

Each animal was dosed daily (IP) with either a test substance or vehicle, starting on Day 0. Beginning on Day 1, acute colon inflammation was induced by the administration ad libitum in drinking water of dextran sulfate sodium (DSS) as a 5% solution in tap water (10 mL/mouse/day for 5–6 days), with no other fluid source for animals in the DSS arm of the study. Filtered tap water was available ad libitum except for animals receiving 5% DSS as the sole source of fluid. After four days, signs of acute disease occured with the loss of weight, diarrhea and bloody stools.

Histological changes included initial shortening of the crypts, then areas of separation of the crypts and the muscularis mucosae in the absence of destructive inflammatory filtrate. After five days, pathological changes became confluent with the appearance of erosions and early hyperplastic epithelium. Inflammation scores were high with neutrophils, lymphocytes, and plasma cells in the *lamina propria* but sparing the epithelium.

Test compounds were administered intraperitoneally (IP). Test compounds given during this period were evaluated for prophylactic activity and test compounds given after the disease state was established were evaluated for therapeutic activity. Ten test animals were assigned to each of ten dose groups listed in Table 6, below.

TABLE 6

Dose group assignments for the DSS-Induced Colitis: Mouse Model of Inflammatory Bowel Disease.

| Group | Test substance | DSS or control |
|---|---|---|
| 1 | Vehicle IP daily | + tap water |
| 2 | Vehicle IP daily | + DSS 5% in tap water |
| 3 | Racemic tofisopam 64 mg/kg IP daily | + DSS 5% in tap water |
| 4 | Racemic tofisopam 32 mg/kg IP daily | + DSS 5% in tap water |
| 5 | Racemic tofisopam 16 mg/kg IP daily | + DSS 5% in tap water |
| 6 | (R)-tofisopam 64 mg/kg IP daily | + DSS 5% in tap water |
| 7 | (R)-tofisopam 32 mg/kg IP daily | + DSS 5% in tap water |
| 8 | (R)-tofisopam 16 mg/kg IP daily | + DSS 5% in tap water |
| 9 | (S)-tofisopam 64 mg/kg IP daily | + DSS 5% in tap water |
| 10 | (S)-tofisopam 32 mg/kg IP daily | + DSS 5% in tap water |
| 11 | (S)-tofisopam 16 mg/kg IP daily | + DSS 5% in tap water |

Test animals were weighed daily from Day 0 to Day 8, or until completion of the study. The total duration of the study with DSS arm of the study was varied depending on the time progress of colitis. The condition of the test animals and consistency of stools was noted.

At the conclusion of the study, test animals were euthanized ($CO_2$), a midline incision was made and a stool sample was obtained. The sample was placed on a slide and tested for occult blood (Quic-Cult™, Laboratory Diagnostics Co., Morganville, N.J.). Occult blood was determined by placing two drops of the reagent onto the sample and observing any color change. Occult blood presence was graded using a scoring protocol assigning a score of 0 for no color; 1 for a very light blue color (+/−) forming in >30 seconds; 2 for a blue color developing in 30 seconds or more (+); 3 for a change in color occurring in less than 30 seconds (++); and 4 for gross blood observable on the slide. The colon was gently stretched and the length from the colon-cecal junction to the end of the distal rectum was measured to the nearest 0.1 cm. A Disease Activity Index (DAI) was determined using the criteria summarized in Table 7 below:

TABLE 7

Scoring criteria for determination of Disease Activity Index (DAI) in the DSS-Induced Colitis: Mouse Model of Inflammatory Bowel Disease.

| Score | Weight loss (%) | Stool consistency | Blood in feces |
|---|---|---|---|
| 0 | 0 or gain | Normal | Negative |
| 1 | 1–4.9 | Soft | +/− |
| 2 | 5.0–9.9 | Mixed soft and diarrhea | + |
| 3 | 10–15 | Diarrhea | ++ |
| 4 | >15 | bloody diarrhea | gross blood |

The scores for each test animal were added and then divided by three to give a DAI score for each animal. The data for the eleven groups is summarized in Tables 8, 9 and 10 below.

TABLE 8

Disease Activity Index for test animals in DSS-induced colitis study.

| Test compound | n | Mean DAI ± SEM | Mean DAI* ± SEM |
|---|---|---|---|
| 0.1% CMC + water | 10 | 0.07 ± 0.04 | 0.00 ± 0.00 |
| 0.1% CMC + DSS | 10 | 2.87 ± 0.24 | 3.25 ± 0.24 |
| Racemic tofisopam 64 mg/kg IP daily | 10 | 2.87 ± 0.31 | 3.25 ± 0.26 |
| Racemic tofisopam 32 mg/kg IP daily | 10 | 2.37 ± 0.33 | 2.65 ± 0.28 |
| Racemic tofisopam 16 mg/kg IP daily | 9 | 2.59 ± 0.27 | 2.61 ± 0.30 |
| (R)-tofisopam 64 mg/kg IP daily | 10 | 1.73 ± 0.27[1] | 2.20 ± 0.26[1] |
| (R)-tofisopam 32 mg/kg IP daily | 10 | 2.33 ± 0.28 | 2.75 ± 0.26 |
| (R)-tofisopam 16 mg/kg IP daily | 9 | 2.22 ± 0.34 | 2.61 ± 0.37 |
| (S)-tofisopam 64 mg/kg IP daily | 9 | 2.78 ± 0.27 | 2.94 ± 0.24 |
| (S)-tofisopam 32 mg/kg IP daily | 10 | 3.07 ± 0.25 | 3.60 ± 0.30 |
| (S)-tofisopam 16 mg/kg IP daily | 10 | 2.37 ± 0.24 | 2.85 ± 0.18 |

[1]Significant difference from vehicle + DSS control - Two-tailed T-test, $p < 0.05$
DAI—Disease Activity Index;
DAI*—DAI without weight loss parameter.

TABLE 9

Colon Length assessment for test animals in DSS-induced colitis study.

| Test compound | n | Mean colon length CM ± SEM | % of normal length | Colon shortening inhib. % |
|---|---|---|---|---|
| 0.1% CMC + water | 10 | 12.5 ± 0.11 | 100 | — |
| 0.1% CMC + DSS | 10 | 7.9 ± 0.18 | 63.5 | — |
| Racemic tofisopam 64 mg/kg IP daily | 10 | 8.2 ± 0.18 | 65.5 | 7 |
| Racemic tofisopam 32 mg/kg IP daily | 10 | 8.3 ± 0.11 | 66.7 | 9 |
| Racemic tofisopam 16 mg/kg IP daily | 10 | 8.2 ± 0.32 | 65.4 | 7 |
| (R)-tofisopam 64 mg/kg IP daily | 10 | 9.8 ± 0.35 | 78.5 | 41[1] |
| (R)-tofisopam 32 mg/kg IP daily | 10 | 8.9 ± 0.41 | 71.3 | 22 |
| (R)-tofisopam 16 mg/kg IP daily | 9 | 9.0 ± 0.28 | 72.4 | 24 |
| (S)-tofisopam 64 mg/kg IP daily | 9 | 8.2 ± 0.20 | 65.4 | 7 |
| (S)-tofisopam 32 mg/kg IP daily | 10 | 8.1 ± 0.19 | 64.9 | 4 |
| (S)-tofisopam 16 mg/kg IP daily | 10 | 8.4 ± 0.19 | 67.3 | 11 |

[1]Significant difference from vehicle + DSS control - $p < 0.05$ One way ANOVA and Tukey-Kramer Multiple Comparisons Test.

TABLE 10

% Weight change for test animals in DSS-induced colitis study.

Mean weight (g) and % weight change ± SEM

| Test Compound | Day 0 | Day 8 | % change | Day 9 | % change | Day 10 | % change |
|---|---|---|---|---|---|---|---|
| 0.1% CMC + water | 26.1 ± 0.4 | 26.5 ± 0.6 | 1.5 ± 1.8 | 26.8 ± 0.6 | 2.7 ± 1.4 | 26.5 ± 0.5 | 1.6 ± 1.3 |
| 0.1% CMC + DSS | 26.1 ± 0.5 | 25.8 ± 0.6 | 1.2 ± 1.3 | 25.0 ± 0.6 | 4.3 ± 0.9 | 24.1 ± 0.6 | 7.7 ± 1.6 |
| Racemic tofisopam 64 mg/kg IP daily | 25.8 ± 0.3 | 25.5 ± 0.7 | 1.2 ± 2.1 | 24.5 ± 0.8 | 5.1 ± 2.5 | 23.5 ± 0.9 | 8.9 ± 3.1 |
| Racemic tofisopam 32 mg/kg IP daily | 26.1 ± 0.4 | 25.6 ± 0.4 | 1.8 ± 1.5 | 24.7 ± 0.6 | 5.3 ± 2.0 | 24.0 ± 0.7 | 8.0 ± 2.4 |
| Racemic tofisopam 16 mg/kg IP daily | 25.9 ± 0.4 | 25.1 ± 0.6 | 3.1 ± 1.5 | 24.0 ± 0.8 | 7.4 ± 2.5 | 22.5 ± 1.0 | 13.3 ± 3.1 |
| (R)-tofisopam 64 mg/kg IP daily | 26.2 ± 0.5 | 26.2 ± 0.5 | 0.1 ± 1.9 | 25.4 ± 0.5 | 2.9 ± 1.9 | 25.4 ± 0.5 | 2.8 ± 2.5 |
| (R)-tofisopam 32 mg/kg IP daily | 25.0 ± 0.4 | 26.2 ± 0.4 | 0.8 ± 1.6 | 25.5 ± 0.6 | 1.9 ± 2.1 | 24.6 ± 0.6 | 4.4 ± 2.1 |
| (R)-tofisopam 16 mg/kg IP daily | 26.1 ± 0.5 | 26.1 ± 0.6 | 0.0 ± 1.4 | 25.2 ± 0.6 | 3.3 ± 1.8 | 24.7 ± 1.0 | 5.4 ± 3.4 |
| (S)-tofisopam 64 mg/kg IP daily | 25.9 ± 0.4 | 25.8 ± 0.6 | 1.2 ± 1.5 | 24.1 ± 0.5 | 6.9 ± 1.8 | 23.2 ± 0.6 | 10.4 ± 1.7 |
| (S)-tofisopam 32 mg/kg IP daily | 25.9 ± 0.4 | 25.1 ± 0.6 | 3.0 ± 0.6 | 24.6 ± 0.6 | 4.9 ± 2.4 | 23.2 ± 0.9 | 10.4 ± 3.2 |
| (S)-tofisopam 16 mg/kg IP daily | 26.0 ± 0.4 | 26.0 ± 0.5 | 0.0 ± 1.5 | 25.6 ± 0.5 | 1.5 ± 1.5 | 24.6 ± 0.6 | 5.4 ± 1.6 |

[1]Significant difference from Vehicle ± DSS group - p < 0.05 - One way ANOVA and Tukey-Kramer Multiple Comparisons Test. Statistical Analysis Incomplete.

The data show that at a dose of 64 mg per kg, (R)-tofisopam provided significant protection from the $LTB_4$-mediated inflammatory responses to DSS-induced colitis. This assessment was based on colon length assessment and an overall Disease Activity Index (DAI) which incorporates scores for indices of colitis progression that include weight loss, stool consistency and amount of detected blood in feces.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A method of treating an individual afflicted with an inflammatory disorder mediated by $LTB_4$ comprising administering to said individual an effective amount of at least one compound according to Formula I:

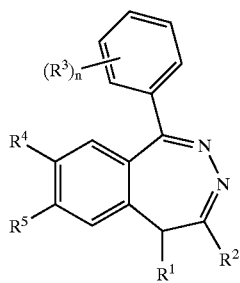

wherein:
$R^1$ is —$(C_1$–$C_7)$hydrocarbyl or —$(C_2$–$C_6)$heteroalkyl;
$R^2$ is selected from the group consisting of —H, and —$(C_1$–$C_7)$hydro-carbyl;
wherein $R^1$ and $R^2$ may combine to form a carbocyclic or heterocyclic 5- or 6-membered ring;

$R^3$ is independently selected from the group consisting of —$O(C_1$–$C_6)$alkyl, —OH, —O-acyl, —SH, —$S(C_1$–$C_3)$alkyl, —$NH_2$, —$NH(C_1$–$C_6)$alkyl, —$N((C_1$–$C_6)$alkyl$)_2$, —NH-acyl, —$NO_2$ and halogen;
n is 1, 2 or 3;
$R^4$ and $R^5$ are independently selected from the group consisting of —$O(C_1$–$C_6)$alkyl, —OH, O-acyl, —SH, —$S(C_1$–$C_3)$alkyl, —$NH_2$, NH-acyl and halogen;
wherein, $R^4$ and $R^5$ may combine to form a 5, 6 or 7-membered heterocyclic ring; and
wherein, compounds according to formula I are (R)-enantiomers substantially free of the corresponding (S)-enantiomers, with respect to the absolute conformation at the 5-position of the benzodiazepine ring;
or a pharmaceutically-acceptable salt of such a compound.

2. The method of claim 1, wherein:
$R^1$ is —$(C_1$–$C_6)$alkyl;
$R^2$ is selected from the group consisting of —H and —$(C_1$–$C_6)$alkyl;
$R^3$ is independently selected from the group consisting of —$O(C_1$–$C_6)$alkyl, —O-acyl and —OH;
n is 1, 2 or 3;
$R^4$ and $R^5$ are independently selected from the group consisting of —$O(C_1$–$C_6)$alkyl, —O-acyl and —OH, wherein, $R^4$ and $R^5$ may combine to form a 5, 6 or 7-membered heterocyclic ring;
or a pharmaceutically-acceptable salt of such a compound.

3. The method of claim 2, wherein:
$R^1$ is —$CH_2CH_3$;
$R^2$ is —$CH_3$
$R^3$, $R^4$ and $R^5$ are independently selected from the group consisting of —OH and —$O(C_1$–$C_6)$alkyl;
n is 1, 2 or 3;
or a pharmaceutically-acceptable salt of such a compound.

4. The method of claim 3, wherein:

$R^1$ is —$CH_2CH_3$;

$R^2$ is —$CH_3$ $R^3$, $R^4$ and $R^5$ are independently selected from the group consisting of —OH and —$OCH_3$;

n is of 1,2 or 3;

or a pharmaceutically-acceptable salt of such a compound.

5. The method of claim 4, wherein the compound is selected from the group consisting of:

(R)-1-(3,4-dimethoxyphenyl)-4-methyl-5-ethyl-7,8-dimethoxy-5H-2,3-benzodiazepine;

(R)-1-(3,4-dimethoxyphenyl)-4-methyl-5-ethyl-7-hydroxy-8-methoxy-5H-2,3-benzodiazepine;

(R)-1-(3-hydroxy-4-methoxyphenyl)-4-methyl-5-ethyl-7,8-dimethoxy-5H-2,3-benzodiazepine;

(R)-1-(3-methoxy-4-hydroxyphenyl)-4-methyl-5-ethyl-7,8-dimethoxy-5H-2,3-benzodiazepine;

(R)-1-(3,4-dimethoxyphenyl)-4-methyl-5-ethyl-7-methoxy-8-hydroxy-5H-2,3-benzodiazepine;

(R)-1-(3-methoxy-4-hydroxyphenyl)-4-methyl-5-ethyl-7-hydroxy-8-methoxy-5H-2,3-benzodiazepine; and (R)-1-(3-hydroxy-4-methoxyphenyl)-4-methyl-5-ethyl-7-hydroxy-8-methoxy-5H-2,3-benzodiazepine;

substantially free of the corresponding (S)-enantiomers;

or a pharmaceutically acceptable salt thereof.

6. The method of claim 5, wherein the compound is (R)-1-(3,4-dimethoxy-phenyl)-4-methyl-5-ethyl-7,8-dimethoxy-5H-2,3-benzodiazepine substantially free of the corresponding (S)-enantiomer;

or a pharmaceutically acceptable salt thereof.

7. The method of claim 1 wherein the disorder is inflammatory bowel disease.

8. The method of claim 1 wherein the disorder is ulcerative colitis.

9. The method of claim 1 wherein the disorder is psoriasis.

10. The method of claim 1 wherein the disorder is rheumatoid arthritis.

11. The method of claim 1 wherein the disorder is Crohn's Disease.

12. The method of claim 1 wherein the disorder is radiation-induced gastrointestinal inflammation.

\* \* \* \* \*